(12) United States Patent
Ferrer et al.

(10) Patent No.: US 7,811,784 B2
(45) Date of Patent: Oct. 12, 2010

(54) TRANSGENIC ORGANISMS WITH LOWER GROWTH TEMPERATURE

(75) Inventors: Manuel Ferrer, Madrid (ES); Kenneth Timmis, Wolfenbüttel (DE); Tatjana Chernikova, Tashkent (UZ); Peter Golyshin, Wolfenbüttel (DE); Michail Yakimov, Messina (IT)

(73) Assignee: Helmholtz-Zentrum für Infektionsforschung GmbH, Braunschweig (DE)

( * ) Notice: Subject to any disclaimer, the term of this patent is extended or adjusted under 35 U.S.C. 154(b) by 934 days.

(21) Appl. No.: 10/575,505

(22) PCT Filed: Oct. 11, 2004

(86) PCT No.: PCT/EP2004/052492

§ 371 (c)(1),
(2), (4) Date: Aug. 29, 2006

(87) PCT Pub. No.: WO2005/035750

PCT Pub. Date: Apr. 21, 2005

(65) Prior Publication Data

US 2009/0255014 A1    Oct. 8, 2009

(30) Foreign Application Priority Data

Oct. 13, 2003    (EP) .................................. 03023032

(51) Int. Cl.
*C12P 21/06*    (2006.01)
*C12N 9/00*    (2006.01)

(52) U.S. Cl. ...................................... 435/69.1; 435/183
(58) Field of Classification Search ....................... None
See application file for complete search history.

(56) References Cited

OTHER PUBLICATIONS

Holland et al. Stress-responsive accumulation of plastid chaperonin 60 during seedling development. (1998) The Plant Journal; vol. 13; pp. 311-316.*
International Search Report.
Database Embl "Online!" "Oleispira Antarctica cpn10 Gene . . . " 2002. XP-002337742 (ISR).
Ferrer et al., "Functional Consequences of Single: Double Ring Transitions in Chaperonins: Life in the Cold," Blackwell Publishing, Ltd., 2004, Molecular Microbiology. vol. 53, No. 1, pp. 167-182. XP-002337729 (ISR).
Tosco et al., "GroEL From the Psychrophilic Bacterium . . . ," Extremophiles, 2003, vol. 7, No. 1, pp. 17-28, XP-002337730 (ISR).
Yamauchi et al., "Gene Structure and Transcriptional regulation specific . . . ," Archives of Microbiology, 2003, vol. 180, No. 4, pp. 272-278. XP-002337731 (ISR).
Yakimov et al., "Oleispira Antarctica Gene . . . " 2003, International Journal of Systematic and Evolutionary Microbiology, vol. 53, No. 3, pp. 779-785. XP-002337732 (ISR).
Walter et al., "Molecular Chaperones—Cellular . . . " Angewandte Chemie, 2002, vol. 41, No. 7, pp. 1098-1113. XP-002337733 (ISR).
Ranson et al., "Chaperonins" Biochemical Journal, 1998, vol. 333, No. 2, pp. 233-242. XP-002337734 (ISR).
Ferrer et al., "Chaperonins Govern Growth . . . " Nature Biotechnology, 2003, vol. 21, No. 11, pp. 1266-1267. XP-009051109 (ISR).
Ferrer et al., "Expression of a Temperature . . . ," Applied and Environmental Microbiology, 2004, vol. 70, No. 8, pp. 4499-4504. XP-002337736 (ISR).
Feller et al., "Expression of Psychrophilic Genes in Mesophilic Hosts . . . ," Applied and Environmental Microbiology, Mar. 1998, vol. 64, No. 3, pp. 1163-1165.
Médigue et al., "Coping with cold: The genome of the versatile . . . ," Genome Research, 2005, pp. 1-12.

* cited by examiner

*Primary Examiner*—Nashaat T Nashed
(74) *Attorney, Agent, or Firm*—Greer, Burns & Crain, Ltd.

(57) ABSTRACT

The invention relates to the growth temperature of organisms, especially plants and microorganisms and the manipulation of the tolerable cultivation temperature. More specifically, the present invention relates to the expression of heterologous proteins in microorganisms, and especially to the heterologous expression of heat sensitive proteins in bacteria, either gram-negative or gram-positive. In a first aspect, the present invention provides a method for manipulation of cells and the resultant cells, wherein at least one gene from a psychrophilic micro organism coding for at least one chaperone or chaperonin is expressed. Such cells are selected among cultivated eukaryotic cells, i.e. animal and plant cells and entire plants, gram-negative and gram-positive bacteria, fungi and yeasts.

8 Claims, 20 Drawing Sheets

Figure 1:

Amino acid sequences of Cpn60 and Cpn10:

SEQ ID No 1: Cpn10 (encoded by nucleotides pos. 458-751 of Figure 2):

MKIRPLHDRIVVRRKEEETATAGGIILPGAAAEKPNQGVVISVGTGRILDNGSVQALA
VNEGDVVVFGKYSGQNTIDIDGEELLILNESDIYGVLEA

SEQ ID No 2: Cpn60 (encoded by nucleotides pos. 800-2446 of Figure 2):

MAAKDVLFGDSARAKMLVGVNILADAVRVTLGPKGRNVVIEKSFGAPIITKDGVSV
AREIELKDKFENMGAQMVKEVASQANDQAGDGTTTATVLAQAIISEGLKSVAAGMN
PMDLKRGIDKATAAVVAAIKEQAQPCLDTKAIAQVGTISANADETVGRLIAEAMEKV
GKEGVITVEEGKGLEDELDVVEGMQFDRGYLSPYFINNQEKMTVEMENPLILLVDKK
IDNLQELLPILENVAKSGRPLLIVAEDVEGQALATLVVNNLRGTFKVAAVKAPGFGD
RRKAMLQDLAILTGGQVISEELGMSLETADPSSLGTASKVVIDKENTVIVDGAGTEAS
VNTRVDQIRAEIESSTSDYDIEKLQERVAKLAGGVAVIKVGAGSEMEMKEKKDRVD
DALHATRAAVEEGVVAGGGVALIRALSSVTVVGDNEDQNVGIALALRAMEAPIRQI
AGNAGAEGSVVVDKVKSGTGSFGFNASTGEYGDMIAMGILDPAKVTRSSLQAAASI
AGLMITTEAMVADAPVEEGAGGMPDMGGMGGMGGMPGMM

Figure 2:

SEQ ID No 3: DNA coding for Cpn60 and Cpn10:

Cpn10, pos. 458-751

Cpn60, pos. 800-2446 atcaaaaaaatgcagcaaggacagattcctgcccaagaattagcagaaggtttcttgttagcactggccggcgctttattattaacgccgg
gttttgtcactgatgcgctgggttttacattactcgtccccgcgacgcgtaaagcgttggtccataaggtgattgcatttattacccctc
gcatgatgactgcaagcagctttcaagcgacgggtagttttcaggaaggctcgtttaaagatgtacattcgcacactgactcgcaaagca
gtcatgaaaaaatcacaattgaaggcgaatataccaaagacgataagtaggtattttttcggctagccgttgaaatcctagtaaaagccc
cgataaattaaccatctattttcacagaggcaatttagcctttgtttaccttattgatcctaatactttgggatccaacagttggagagtctagc
aaatgaaaatccgtccattacatgatcgtattgttgttcgccgtaaagaagaagagaccgcaactgcggggtggtattatttttacc
gggcgctgcggcagaaaaaaccaaatcaaggtgttgttatctctgtgggtactggccgtattcttgataatggttcagtgcaagcgctggc
ggttaacgaaggcgatgttgtcgttttggtaaatactcaggtcaaaatactatcgatatcgatggtgaagaattattgatttgaatga
agtgatatctacggcgttttagaagcttaattattacactcactttttatttaacctacaaaatttaaggaaagatcatggctgctaaagacg
tattattggtgatagcgcacgcgcaaaaatgttggtaggtgtaaacattttagccgacgcagtaagagttaccttaggacctaa
aggtcgtaacgttgttatagaaaaatcattggtgcaccgatcatcaccaaagatggtgtttctgttgcgcgtgaaatcgaattgaaagaca
aattcgaaaacatgggcgcacagatggttaaggaagttgcttctcaagccaacgaccaagccggtgacggcacaacgacagcgact
gtactagcacaggcgattatcagcgaaggcttgaaatctgttgcggctggcatgaatccaatggatcttaaacgtggtattgataaagcta
cggctgctgttgttgccgccattaaagaacaagctcagccttgcttggatacaaaagcaatcgctcaggtagggacaatctctgccaatg
ccgatgaaacggttggtcgtttaattgctgaagcgatggaaaaagtcggtaaagaaggtgtgattaccgttgaagaaggcaaaggcctt
gaagacgagcttgatgttgtagaaggcatgcagttcgatcgcggttacttgtctccgtacttcatcaacaaccaagaaaaaatgaccgta
gaaatggaaaatccattaatctattggttgataagaaaattgataaccttcaagagctgttgccaattcttgaaaacgtcgctaaatcaggt
cgtccattattgatcgttgctgaagatgttgaaggccaagcactagcaacattggtagtaaacaacttgcgcggcacattcaaggttgc
agcggttaaagcccctggttttggcgatcgtcgtaaagcgatgttgcaagatcttgccatcttgacgggtggtcaggttatttctgaagag
ctagggatgtctttagaaactgcggatccttcttcttgggtacggcaagcaaggttgttatcgataaagaaaacaccgtgattgttga
tggcgcaggtactgaagcaagcgttaatactcgtgttgaccagatccgtgctgaaatcgaaagctcgacttctgattacgacatcgaaaa
gttacaagaacgcgttgctaagcttgcgggcggcgttgccgtgattaaggttggtgcgggttctgaaatggaaatgaaagagaagaaa
gaccgtgttgacgatgcacttcatgcaactcgcgcagcggttgaagaaggtgttgttgcgggtggtggtgttgctttgattcgcgcactct
cttcagtaaccgttgttggtgataacgaagatcaaaacgtcggtattgcattggcacttcgtgcgatggaagctcctatccgtcaaatcgc
gggtaacgcaggtgctgaagggtcagtggttgttgataaagtgaaatctggcacaggtagctttggttttaacgccagcacaggtgagt
atggcgatatgattgcgatgggtatttagacccctgcaaaagtcacgcgttcatctctacaagccgcggcgtctatcgcaggtttgatgat

Figure 2 (continued):

cacaaccgaagccatggttgcggatgcgcctgttgaagaaggcgctggtggtatgcctgatatgggcggcatgggtggaatgggcg gtatgcctggcatgatgtaatcactttgtgattcattgtcctgatctgcttaccgtgtaaaaagatcaggctcaaggctgtctctataaaaag ccgtatctttgatgagtgttgtctttctgctgaaaacgacattcttggagtgcggcttttttgatttggtcataaaattcagaatattgtgtaatt ttatgtaactagctggcctataatgttgagttcctctggggtggcatgatctcatggtacttcacttaagcctgattcactgcg gctttaacagtaaaataataacgcaacgtagaaacataataagcgtatggcattaatgaagacggctgcatttaattcagatc

Figure 3:

SEQ ID No 4: Amino acid sequence of esterase cloned from *Oleispira antarctica* (EstRB8):

EstRB8 (encoded by nucleotides 1145 to 2143 Frame 2 of Figure 4) 333 aa
MKNTLKSSSRFSLKQLGTGALIISSLFFGGCTTTQQDNLYTGVMSLARDSAGLEVKTA
SAGDVNLTYMERQGSDKDNAESVILLHGFSADKDNWILFTKEFDEKYHVIAVDLAG
HGDSEQLLTTDYGLIKQAERLDIFLSGLGVNSFHIAGNSMGGAISAIYSLSHPEKVKSL
TLIDAAGVDGDTESEYYKVLAEGKNPLIATDEASFEYRMGFTMTQPPFLPWPLRPSLL
RKTLARAEINNKIFSDMLKTKERLGMTNFQQKIEVKMAQHPLPTLIMWGKEDRVLD
VSAAAAFKKHPQATVHIFPEVGHLPMVEIPSESAKVYEEFLSSIK

Figure 4:

SEQ ID No 5: DNA fragment from plasmid pBK1Est coding for esterase of *Oleispira antarctica* (EstRB8):

Nucleotide positions 1-100 correspond to reverse complement of positions 1196-1121 and 3799-3939 correspond to reverse complement of 1043-952 of pBK-CMV vector (Stratagene).

Positions 101-105 are BamHI – Sau3A1 fusion and positions 3795-3798 are Sau3A1-BamHI-fusion.

acaggaaacagctatgaccttgattacgccaagctcgaaattaaccctcactaaagggaacaaaagctggagctcgcgcgcctgcag
gtcgacactagtggatcaacggcgttcatggtactggctgagttcagcgtcataatgccgatgcgatactggccgtcatgactgagtact
tcttctgctagcaccgatttttctaatagcgcagcttctttttatttctgaacgggcaactgatgtagttttttactaaccggcttttttaggcatgg
taaactcttcgatattcaaaattattactgttcatattacaatcatagtacaggctagaggcccaaaattgcagctgatattcacctttattattc
taagcattattacactcatcgcggtgttattaattgtgctaaataaaatacccgtagcggaaaaattcagcaaatagccaagaaaacga
ttggcaataccaagaattcatcgatttgatgatgacattaagcaggcaaactttggcctattaaactacagtcaaaatgcaatttttagacat
ctcattcaagcaactgacgaacactatggcttagcgtttaagacctttgactgtcgagcgttagaaccttcaggtattcacaatagcagtct
tatttatttaccctcgcactaaagactgaattcaataacctacacatttgcttaagtcgacatatcaagataaagatgccttcactgacatca
gtcaccaacaatcaatcaaacaccaataccaatcgcaaaaactcataaaactagccgatcaccaaatcccaaaagcgttcaaaaatgaa
acgagcacgtcacacaaaatcaatttatacgctaacgaaccaggtcaaacttatcgtttttttgagcacgtttgttccactaatgaaagaga
aaagtcgttaattcactggcttttggcgtatccgcaccttcacatagaaattagtaatggcatgctactggcctttaaaaagaatcagttaatt
gaagaaacctcgcttatctcagccattaccgctgtagccgaatttgcgcttatcctcagccatgattaaactgacgccaattaatataagac
atactaattaataactccctttaattgagaagaataatgaaaaacacactcaaatcctcatcacgttttagtctgaaacaactcggcaccggc
gctctgattatctccagttttgttcttcggtggttgcaccacaacacaacaagataatttatacacaggggttatgtctcttgcgagagacagc
gctggcctagaagttaaaacagcctctgccggtgacgtcaatcttacttatatggaacgccaaggcagtgacaaagataatgccgaaag
cgttatttttattacacggtttctctgctgataaagataactggattcttttaccaaagaattcgatgaaaaatatcatgttatcgctgtcgattta
gcgggacatggccgattcagaacaattattaacgactgattacgtctcataaaacaagccgagcgtttagatatcttcttatctggcttagg
ggttaactcatttcacatcgccggtaattcaatgggggggggctatcagcgcaatctacagtttgagtcacccagagaaagttaaaagtctt
acattgatcgatgcagcaggtgtcgatggcgatactgaaagcgaatactacaaagttttggcagaaggtaagaatcctttaattgcaact
gatgaagcaagttttgaataccgcatgggtttcaccatgactcagcctccttcctaccttggccactaagaccttcttattacgtaaaacg
ctagcccgtgccgagatcaataacaaaattttttccgatatgctgaaaaccaaagaacgtttaggaatgactaactttcaacagaaaattg
aagtgaaaatggctcaacatccattgccaacactgattatgtggggcaaagaagatcgcgttcttgacgtatccgcagcagcggcctc
aaaaaaataattccacaagcaactgttcatattttcctgaagtaggccacctacctatggtagaaattcctagtgaaagcgctaaagtttat

Figure 4 (continued):

gaagagtttttgtcctctattaaataagagcacataatcatgactgacttataaacagccaagcatttaaaatgcttggctgtttatttttaatgg
ccaaattattcaacgaccaagctctgcggtaaaatcgcagtgggtttcttgttttcatcaacagcaacaaacgtgaaataccccgtaatcg
cattttctgattatcaaaatacatactttccaccagcatattaacttcaacttttaaactcgtccgccctacctctataacactggcagtcaatt
cgacaatggtacctgcgggaacaggatgcttaaaatcgattcgatcactgctgacggttacgatgctttgtcgagaaaaacgagtcgct
gcaataaaagaaacctcatccatccactgcattgcagtgccaccgaataacgtatcatgatgatttgttgtctctggaaataccgctttaga
aatagtggttttgatacgcgctttcgctgcgcaataatatcttctctgctaagagttgcggatggcatacataaactcgcttgattaagatta
ataataaatagttaacagtatattgaactgagggtctgaagaactctaaatacctctgaagaactttgaggccgctagagagaaaagacca
gtgataatatttcatcttgccatgagagcttatcatgaaagcctgtgcttaaaatcaatcattatatttattcatctttaattgaaataataccaat
atatttcatatataatttcacactacccttatctcactagacttcccgcgcataggcgcaaacaatcaacgcaagttcacaataaagcggttc
gctgcaacacatgccctagcgtctaaagtagcacgcacaacactggccagtcgtactagccccttgcgattcgtgcagacgagcaac
aagcgctattaaactacctaaattctaaccaccaccattggttctttccacaaactcaaaaaactcgtcaaatccgcttgcaatttaaacg
cgatgacatagatctaatcgattatcaaaccccgcattcaagcgctcattaaaaacgcaccactggcaagaagttctacctgcactgacca
atatgcaagcggcggcggaagagctgcctttgatcgatcaagaagaagggagcagcaaagaggaaaacaatcaaaaagaggaga
gcaatcaaataaaaacgagttattgaggattttaattttaaaacaggtatattaatacccctctctcgtagtaaacaatgactgtatttacacaa
aaataaatagaggtataccatgtcaaacatctggtttgaagtaccaaagattgaagtattaaaccgtcaaatggaaaatactgcctgcagc
aacttaggcattcaaattacagaaattggcgatgattatatcactggcacaatgccagcagatgcacgtaccttccagccaatgggactg
attcatggcggctcaaatgtattgctggcagaaacactgggcagcatggcagctaactgctgtattaatttgtctcaagaatattgtgttgg
ccaagaaattaacgccaaccacatacgcggtgttcgttccggcatagtgactggcacagcaacgctagtacacaaaggaagaacctc
ccagatttgggaaattcgcatcgttaacgatccaaagaattcaaaaagcttctcgagagtactctagagcggccgcgggcccatcgatt
ttccacccgggtggggtaccaggtaagtgtacccaattcgccctatagtgagtcgtattacaattcactggccgtcgttttac

Figure 5:

Amino acid sequences expressed from vector pBK1CpnEst: - the co-expression of fragments encoding native chaperonines with the esterase gene (EstRB8), all from *Oleispira antarctica*

SEQ ID No 6: cpn10 (nucleotides 113 to 403: Frame 2 of Figure 6) 97 aa:

MKIRPLHDRIVVRRKEEETATAGGIILPGAAAEKPNQGVVISVGTGRILDNGSVQALA
VNEGDVVVFGKYSGQNTIDIDGEELLILNESDIYGVLEA

SEQ ID No 7: cpn60 (nucleotides 455 to 2098: Frame 2 of Figure 6) 548 aa:

MAAKDVLFGDSARAKMLVGVNILADAVRVTLGPKGRNVVIEKSFGAPIITKDGVSV
AREIELKDKFENMGAQMVKEVASQANDQAGDGTTTATVLAQAIISEGLKSVAAGMN
PMDLKRGIDKATAAVVAAIKEQAQPCLDTKAIAQVGTISANADETVGRLIAEAMEKV
GKEGVITVEEGKGLEDELDVVEGMQFDRGYLSPYFINNQEKMTVEMENPLILLVDKK
IDNLQELLPILENVAKSGRPLLIVAEDVEGQALATLVVNNLRGTFKVAAVKAPGFGD
RRKAMLQDLAILTGGQVISEELGMSLETADPSSLGTASKVVIDKENTVIVDGAGTEAS
VNTRVDQIRAEIESSTSDYDIEKLQERVAKLAGGVAVIKVGAGSEMEMKEKKDRVD
DALHATRAAVEEGVVAGGGVALIRALSSVTVVGDNEDQNVGIALALRAMEAPIRQI
AGNAGAEGSVVVDKVKSGTGSFGFNASTGEYGDMIAMGILDPAKVTRSSLQAAASI
AGLMITTEAMVADAPVEEGAGGMPDMGGMGGMGGMPGMM

SEQ ID No 8: estRB8 (nucleotides 2579 to 3577: Frame 2 of Figure 6) 333 aa:

MKNTLKSSSRFSLKQLGTGALIISSLFFGGCTTTQQDNLYTGVMSLARDSAGLEVKTA
SAGDVNLTYMERQGSDKDNAESVILLHGFSADKDNWILFTKEFDEKYHVIAVDLAG
HGDSEQLLTTDYGLIKQAERLDIFLSGLGVNSFHIAGNSMGGAISAIYSLSHPEKVKSL
TLIDAAGVDGDTESEYYKVLAEGKNPLIATDEASFEYRMGFTMTQPPFLPWPLRPSLL
RKTLARAEINNKIFSDMLKTKERLGMTNFQQKIEVKMAQHPLPTLIMWGKEDRVLD
VSAAAAFKKIIPQATVHIFPEVGHLPMVEIPSESAKVYEEFLSSIK

Figure 6:

SEQ ID No 9: pBK1CpnEst: - the fusion of native chaperonine-coding fragments with esterase of *Oleispira antarctica* (EstRB8)

The DNA fragment coding for Cpn10 and Cpn60 is flanked by *SacI* site (pos. 69-75) and *SalI* site (encoded by pos. 2138-2143 of Figure 7):

Nucleotide positions 1-75 correspond to reverse complement of positions 1196-1121 and positions 5233-5273 correspond to reverse complement of 1043-952 of pBK-CMV vector (Stratagene)

Small letters – the Cpn10-Cpn60 encoding fragment,
Capital italics – fragments of vector pBK-CMV
Capital letters – fragment coding for EstRB8 from plasmid pBK1Est

*ACAGGAAACAGCTATGACCTTGATTACGCCAAGCTCGAAATTAACCCTCACTAAAGGGA*
*ACAAAAGCTGGAGCT*ctaatacttgggatccaacagttggagagtctagcaaatgaaaatccgtccattacatgatcgtatt
gttgttcgccgtaaagaagaagagaccgcaactgcggggtggtattatttttaccgggcgctgcggcagaaaaaccaaatcaaggtgttgt
tatctctgtgggtactggccgtattcttgataatggttcagtgcaagcgctggcggttaacgaaggcgatgttgtcgttttttggtaaatactc
aggtcaaaatactatcgatatcgatggtgaagaattattgattttgaatgaaagtgatatctacggcgttttagaagcttaattattacactca
ctttttatttaacctacaaaatttaaggaaagatcatggctgctaaagacgtattatttggtgatagcgcacgcgcaaaaatgttggtaggt
gtaaacatttagccgacgcagtaagagttaccttaggacctaaaggtcgtaacgttgttatagaaaaatcatttggtgcaccgatcatcac
caaagatggtgtttctgttgcgcgtgaaatcgaattgaaagacaaaatcgaaaacatgggcgcacagatggttaaggaagttgcttctca
agccaacgaccaagccggtgacggcacaacgacagcgactgtactagcacaggcgattatcagcgaaggcttgaaatctgttgcgg
ctggcatgaatccaatggatcttaaacgtggtattgataaagctacggctgctgttgttgccgccattaaagaacaagctcagccttgcttg
gatacaaaagcaatcgctcaggtagggacaatctctgccaatgccgatgaaacggttggtcgtttaattgctgaagcgatggaaaaagt
cggtaaagaaggtgtgattaccgttgaagaaggcaaaggccttgaagacgagcttgatgttgtagaaggcatgcagttcgatcgcggtt
acttgtctccgtacttcatcaacaaccaagaaaaaatgaccgtagaaatggaaaatccattaattctattggttgataagaaaattgataac
cttcaagagctgttgccaattcttgaaaacgtcgctaaatcaggtcgtccattattgatcgttgctgaagatgttgaaggccaagcactagc
aacattggtagtaaacaactgcgcggcacattcaaggttgcagcggttaaagcccctggttttggcgatcgtcgtaaagcgatgttgca
agatcttgccatcttgacgggtggtcaggttatttctgaagagctagggatgtctttagaaactgcggatccttcttcttttgggtacggcaa
gcaaggttgttatcgataaagaaaacaccgtgattgttgatggcgcaggtactgaagcaagcgttaatactcgtgttgaccagatccgtg
ctgaaatcgaaagctcgacttctgattacgacatcgaaaagttacaagaacgcgttgctaagcttgcggggcggcgttgccgtgattaag

Figure 6 (continued):

gttggtgcgggttctgaaatggaaatgaaagagaagaaagaccgtgttgacgatgcacttcatgcaactcgcgcagcggttgaagaag
gtgttgttgcgggtggtggtgttgcttgattcgcgcactctcttcagtaaccgttgttggtgataacgaagatcaaaacgtcggtattgcat
tggcacttcgtgcgatggaagctcctatccgtcaaatcgcgggtaacgcaggtgctgaagggtcagtggttgttgataaagtgaaatctg
gcacaggtagctttggttttaacgccagcacaggtgagtatggcgatatgattgcgatgggtattttagaccctgcaaaagtcacgcgttc
atctctacaagccgcggcgtctatcgcaggtttgatgatcacaaccgaagccatggttgcggatgcgcctgttgaagaaggcgctggtg
gtatgcctgatatgggcggcatgggtggaatgggcggtatgcctggcatgatgtaatcactttgtgattcattgtcctgatctgcttaccgt
GTCGACATATTCAAGATAAAGATGCCTTCACTGACATCAGTCACCAACAATCAAT
CAAACACCAATACCAATCGCAAAAACTCATAAAACTAGCCGATCACCAAATCCC
AAAAGCGTTCAAAAATGAAACGAGCACGTCACACAAAATCAATTTATACGCTAA
CGAACCAGGTCAAACTTATCGTTTTTTTGAGCACGTTTGTTCCACTAATGAAAGA
GAAAAGTCGTTAATTCACTGGCTTTTGGCGTATCCGCACCTTCACATAGAAATTA
GTAATGGCATGCTACTGGCCTTTAAAAAGAATCAGTTAATTGAAGAAACCTCGCT
TATCTCAGCCATTACCGCTGTAGCCGAATTTGCGCTTATCCTCAGCCATGATTAAA
CTGACGCCAATTAATATAAGACATACTAATTAATAACTCCCTTAATTGAGAAGAA
TAATGAAAAACACACTCAAATCCTCATCACGTTTAGTCTGAAACAACTCGGCAC
CGGCGCTCTGATTATCTCCAGTTTGTTCTTCGGTGGTTGCACCACAACACAACAAG
ATAATTTATACACAGGGGTTATGTCTCTTGCGAGAGACAGCGCTGGCCTAGAAGT
TAAAACAGCCTCTGCCGGTGACGTCAATCTTACTTATATGGAACGCCAAGGCAGT
GACAAAGATAATGCCGAAAGCGTTATTTTATTACACGGTTTCTCTGCTGATAAAG
ATAACTGGATTCTTTTTACCAAAGAATTCGATGAAAAATATCATGTTATCGCTGTC
GATTTAGCGGGACATGGCGATTCAGAACAATTATTAACGACTGATTACGGTCTCA
TAAAACAAGCCGAGCGTTTAGATATCTTCTTATCTGGCTTAGGGGTTAACTCATTT
CACATCGCCGGTAATTCAATGGGGGGGGCTATCAGCGCAATCTACAGTTTGAGTC
ACCCAGAGAAAGTTAAAAGTCTTACATTGATCGATGCAGCAGGTGTCGATGGCG
ATACTGAAAGCGAATACTACAAAGTTTTGGCAGAAGGTAAGAATCCTTTAATTGC
AACTGATGAAGCAAGTTTTGAATACCGCATGGGTTTCACCATGACTCAGCCTCCT
TTCCTACCTTGGCCACTAAGACCTTCTTTATTACGTAAAACGCTAGCCCGTGCCGA
GATCAATAACAAAATTTTTTCCGATATGCTGAAAACCAAAGAACGTTTAGGAATG
ACTAACTTTCAACAGAAAATTGAAGTGAAAATGGCTCAACATCCATTGCCAACAC
TGATTATGTGGGGCAAAGAAGATCGCGTTCTTGACGTATCCGCAGCAGCGGCCTT
CAAAAAAATAATTCCACAAGCAACTGTTCATATTTTCCTGAAGTAGGCCACCTA

Figure 6 (continued):

CCTATGGTAGAAATTCCTAGTGAAAGCGCTAAAGTTTATGAAGAGTTTTGTCCT
CTATTAAATAAGAGCACATAATCATGACTGACTTATAAACAGCCAAGCATTTAAA
ATGCTTGGCTGTTTATTTTAATGGCCAAATTATTCAACGACCAAGCTCTGCGGTAA
AATCGCAGTGGGTTTCTTGTTTTCATCAACAGCAACAAACGTGAAATACCCCGTA
ATCGCATTTTTCTGATTATCAAAATACATACTTTCCACCAGCATATTAACTTCAAC
TTTTAAACTCGTCCGCCCTACCTCTATAACACTGGCAGTCAATTCGACAATGGTAC
CTGCGGGAACAGGATGCTTAAAATCGATTCGATCACTGCTGACGGTACGATGCT
TTGTCGAGAAAAACGAGTCGCTGCAATAAAAGAAACCTCATCCATCCACTGCATT
GCAGTGCCACCGAATAACGTATCATGATGATTTGTTGTCTCTGGAAATACCGCTTT
AGAAATAGTGGTTTTTGATACGCGCTTTCGCTGCGCAATAATATCTTCTCTGCTAA
GAGTTGCGGATGGCATACATAAACTCGCTTGATTAAGATTAATAATAAATAGTTA
ACAGTATATTGAACTGAGGGTCTGAAGAACTCTAATACCTCTGAAGAACTTTGAG
GCCGCTAGAGAGAAAGACCAGTGATAATATTTCATCTTGCCATGAGAGCTTATC
ATGAAAGCCTGTGCTTAAAATCAATCATTATATTTATTCATCTTTAATTGAAATAA
TACCAATATATTTCATATATAATTTCACACTACCCTTATCTCACTAGACTTCCCGC
GCATAGGCGCAAACAATCAACGCAAGTTCACAATAAAGCGGTTCGCTGCAACAC
ATGCCCTAGCGTCTAAAGTAGCACGCACAACACTGGCCAGTCGTACTAGCCCCTT
TGCGATTCGTGCAGACGAGCAACAAGCGCTATTAAACTTACCTAAATTTCTAACC
ACCACCATTGGTTCTTTTCCACAAACTCAAAAAACTCGTCAAATCCGCTTGCAATT
TAAACGCGATGACATAGATCTAATCGATTATCAAACCCGCATTCAAGCGCTCATT
AAAAACGCACCACTGGCAAGAAGTTCTACCTGCACTGACCAATATGCAAGCGGC
GGCGGAAGAGCTGCCTTTGATCGATCAAGAAGAAGGGAGCAGCAAAGAGGAAA
ACAATCAAAAGAGGAGAGCAATCAAATAAAAACGAGTTATTGAGGATTTTAAT
TTTAAAACAGGTATATTAATACCCTCTCTCGTAGTAAACAATGACTGTATTTACAC
AAAAATAAATAGAGGTATACCATGTCAAACATCTGGTTTGAAGTACCAAAGATTG
AAGTATTAAACCGTCAAATGGAAAATACTGCCTGCAGCAACTTAGGCATTCAAAT
TACAGAAATTGGCGATGATTATATCACTGGCACAATGCCAGCAGATGCACGTACC
TTCCAGCCAATGGGACTGATTCATGGCGGCTCAAATGTATTGCTGGCAGAAACAC
TGGGCAGCATGGCAGCTAACTGCTGTATTAATTTGTCTCAAGAATATTGTGTTGG
CCAAGAAATTAACGCCAACCACATACGCGGTGTTCGTTCCGGCATAGTGACTGGC
ACAGCAACGCTAGTACACAAAGGAAGAACCTCCCAGATTTGGGAAATTCGCATC

Figure 6 (continued):

GTTAACGATCCAAAGAATTCAAAAAGCTTCTCGAGAGTACTTCTAGAGCGGCCGCGGG
CCCATCGATTTTCCACCCGGGTGGGGTACCAGGTAAGTGTACCCAATTCGCCCTATAGT
GAGTCGTATTACAATTCACTGGCCGTCGTTTTAC

Figure 7:

Amino acid sequences expressed from vector pBK1CpnSREst: - the co-expression of the stabilized single ring mutant chaperonin with the esterase gene (EstRB8) from *Oleispira antarctica* (cpn10::stabilized single ring mutant Glu460Ala/Ser462Ala/Val463Ala::est)

SEQ ID No 10: cpn10 (nucleotides 113 to 403; Frame 2 of Figure 8) 97 aa:

MKIRPLHDRIVVRRKEEETATAGGIILPGAAAEKPNQGVVISVGTGRILDNGSVQALA
VNEGDVVVFGKYSGQNTIDIDGEELLILNESDIYGVLEA

Below – *Capital bold letters* are the mutations introduced

SEQ ID No 11: stabilized single ring mutant of cpn60 (nucleotides 455 to 2098; Frame 2 of Figure 8) 548 aa:

MAAKDVLFGDSARAKMLVGVNILADAVRVTLGPKGRNVVIEKSFGAPIITKDGVSV
AREIELKDKFENMGAQMVKEVASQANDQAGDGTTTATVLAQAIISEGLKSVAAGMN
PMDLKRGIDKATAAVVAAIKEQAQPCLDTKAIAQVGTISANADETVGRLIAEAMEKV
GKEGVITVEEGKGLEDELDVVEGMQFDRGYLSPYFINNQEKMTVEMENPLILLVDKK
IDNLQELLPILENVAKSGRPLLIVAEDVEGQALATLVVNNLRGTFKVAAVKAPGFGD
RRKAMLQDLAILTGGQVISEELGMSLETADPSSLGTASKVVIDKENTVIVDGAGTEAS
VNTRVDQIRAEIESSTSDYDIEKLQERVAKLAGGVAVIKVGAGSEMEMKEKKDRVD
DALHATRAAVEEGVVAGGGVALIRALSSVTVVGDNEDQNVGIALALRAMEAPIRQI
AGNAGAAGAAVVDKVKSGTGSFGFNASTGEYGDMIAMGILDPAKVTRSSLQAAASI
AGLMITTEAMVADAPVEEGAGGMPDMGGMGGMGGMPGMM

SEQ ID No 12: EstRB8 (nucleotides 2579 to 3577; Frame 2 of Figure 8) 333 aa:

MKNTLKSSSRFSLKQLGTGALIISSLFFGGCTTTQQDNLYTGVMSLARDSAGLEVKTA
SAGDVNLTYMERQGSDKDNAESVILLHGFSADKDNWILFTKEFDEKYHVIAVDLAG
HGDSEQLLTTDYGLIKQAERLDIFLSGLGVNSFHIAGNSMGGAISAIYSLSHPEKVKSL

Figure7 (continued):

TLIDAAGVDGDTESEYYKVLAEGKNPLIATDEASFEYRMGFTMTQPPFLPWPLRPSLL
RKTLARAEINNKIFSDMLKTKERLGMTNFQQKIEVKMAQHPLPTLIMWGKEDRVLD
VSAAAAFKKHPQATVHIFPEVGHLPMVEIPSESAKVYEEFLSSIK

Figure 8:

SEQ ID No 13: DNA sequence of vector pBK1CpnSREst: the expression cassette for the co-expression of the stabilized single ring mutant chaperonin with the esterase gene (EstRB8) from *Oleispira antarctica* (cpn10::stabilized single ring mutant Glu460Ala/Ser462Ala/Val463Ala::est)

Nucleotide positions 1-75 correspond to reverse complement of positions 1196-1121 and positions 5233-5273 correspond to reverse complement of 1043-952 of pBK-CMV vector (Stratagene)

DNA fragment coding for Cpn10 and Cpn60 is flanked by *SacI* site (pos. 69-75) and *SalI* site (pos. 2138-2143).

In the DNA sequence:
Small letters – the Cpn10-Cpn60 coding fragment,
Capital italics – fragments of vector
Capital letters – fragment coding for EstRB8 from plasmid pBK1Est
Capital bold letters = introduced mutations

*ACAGGAAACAGCTATGACCTTGATTACGCCAAGCTCGAAATTAACCCTCACTAAAGGGA*
*ACAAAAGCTGGAGCTC*ctaatacttgggatccaacagttggagagtctagcaaatgaaaatccgtccattacatgatcgtatt
gttgttcgccgtaaagaagaagagaccgcaactgcggqtggtattatttaccgggcgctgcggcagaaaaaccaaatcaaggtgttgt
tatctctgtgggtactggccgtattcttgataatggttcagtgcaagcgctggcggttaacgaaggcgatgttgtcgtttttggtaaatactc
aggtcaaaatactatcgatatcgatggtgaagaattattgattttgaatgaaagtgatatctacggcgtttagaagcttaattattacactca
cttttttatttaacctacaaaatttaaggaaagatcatggctgctaaagacgtattatttggtgatagcgcacgcgcaaaaatgttggtaggt
gtaaacattttagccgacgcagtaagagttacctaggacctaaaggtcgtaacgttgttatagaaaaatcatttggtgcaccgatcatcac
caaagatggtgtttctgttgcgcgtgaaatcgaattgaaagacaaattcgaaaacatgggcgcacagatggttaaggaagttgcttctca
agccaacgaccaagccggtgacggcacaacgacagcgactgtactagcacaggcgattatcagcgaaggcttgaaatctgttgcgg
ctggcatgaatccaatggatcttaaacgtggtattgataaagctacggctgctgttgttgccgccattaaagaacaagctcagccttgcttg
gatacaaaagcaatcgctcaggtagggacaatctctgccaatgccgatgaaacggttggtcgtttaattgctgaagcgatggaaaaagt
cggtaaagaaggtgtgattaccgttgaagaaggcaaaggccttgaagacgagcttgatgttgtagaaggcatgcagttcgatcgcggtt
acttgtctccgtacttcatcaacaaccaagaaaaaatgaccgtagaaatggaaaatccattaattctattggttgataagaaaattgataac
cttcaagagctgttgccaattcttgaaaacgtcgctaaatcaggtcgtccattattgatcgttgctgaagatgttgaaggccaagcactagc*

Figure 8 (continued):

aacattggtagtaaacaacttgcgcggcacattcaaggttgcagcggttaaagcccctggttttggcgatcgtcgtaaagcgatgttgca
agatcttgccatcttgacgggtggtcaggttatttctgaagagctagggatgtctttagaaactgcggatccttcttctttgggtacggcaa
gcaaggttgttatcgataaagaaaacaccgtgattgttgatggcgcaggtactgaagcaagcgttaatactcgtgttgaccagatccgtg
ctgaaatcgaaagctcgacttctgattacgacatcgaaaagttacaagaacgcgttgctaagcttgcgggcggcgttgccgtgattaag
gttggtgcgggttctgaaatggaaatgaaagagaagaaagaccgtgttgacgatgcacttcatgcaactcgcgcagcggttgaagaag
gtgttgttgcgggtggtggtgttgctttgattcgcgcactctcttcagtaaccgttgttggtgataacgaagatcaaaacgtcggtattgcat
tggcacttcgtgcgatggaagctcctatccgtcaaatcgcgggtaacgcaggtgctgCagggGcagCggttgttgataaagtgaaat
ctggcacaggtagctttggttttaacgccagcacaggtgagtatggcgatatgattgcgatgggtattttagaccctgcaaaagtcacgc
gttcatctctacaagccgcggcgtctatcgcaggtttgatgatcacaaccgaagccatggttgcggatgcgcctgttgaagaaggcgct
ggtggtatgcctgatatgggcggcatgggtggaatgggcggtatgcctggcatgatgtaatcactttgtgattcattgtcctgatctgctta
ccgtGTCGACATATTCAAGATAAAGATGCCTTCACTGACATCAGTCACCAACAATC
AATCAAACACCAATACCAATCGCAAAAACTCATAAAACTAGCCGATCACCAAAT
CCCAAAAGCGTTCAAAAATGAAACGAGCACGTCACACAAAATCAATTTATACGC
TAACGAACCAGGTCAAACTTATCGTTTTTTTGAGCACGTTTGTTCCACTAATGAAA
GAGAAAAGTCGTTAATTCACTGGCTTTTGGCGTATCCGCACCTTCACATAGAAAT
TAGTAATGGCATGCTACTGGCCTTTAAAAAGAATCAGTTAATTGAAGAAACCTCG
CTTATCTCAGCCATTACCGCTGTAGCCGAATTTGCGCTTATCCTCAGCCATGATTA
AACTGACGCCAATTAATATAAGACATACTAATTAATAACTCCCTTAATTGAGAAG
AATAATGAAAAACACACTCAAATCCTCATCACGTTTTAGTCTGAAACAACTCGGC
ACCGGCGCTCTGATTATCTCCAGTTTGTTCTTCGGTGGTTGCACCACAACACAACA
AGATAATTTATACACAGGGGTTATGTCTCTTGCGAGAGACAGCGCTGGCCTAGAA
GTTAAAACAGCCTCTGCCGGTGACGTCAATCTTACTTATATGGAACGCCAAGGCA
GTGACAAAGATAATGCCGAAAGCGTTATTTTATTACACGGTTTCTCTGCTGATAA
AGATAACTGGATTCTTTTTACCAAAGAATTCGATGAAAAATATCATGTTATCGCT
GTCGATTTAGCGGGACATGGCGATTCAGAACAATTATTAACGACTGATTACGGTC
TCATAAAACAAGCCGAGCGTTTAGATATCTTCTTATCTGGCTTAGGGGTTAACTC
ATTTCACATCGCCGGTAATTCAATGGGGGGGGCTATCAGCGCAATCTACAGTTTG
AGTCACCCAGAGAAAGTTAAAAGTCTTACATTGATCGATGCAGCAGGTGTCGATG
GCGATACTGAAAGCGAATACTACAAAGTTTTGGCAGAAGGTAAGAATCCTTTAAT
TGCAACTGATGAAGCAAGTTTTGAATACCGCATGGGTTTCACCATGACTCAGCCT
CCTTTCCTACCTTGGCCACTAAGACCTTCTTTATTACGTAAAACGCTAGCCCGTGC
CGAGATCAATAACAAAATTTTTTCCGATATGCTGAAAACCAAAGAACGTTTAGGA Figure 8 (continued):

ATGACTAACTTTCAACAGAAAATTGAAGTGAAAATGGCTCAACATCCATTGCCAA
CACTGATTATGTGGGGCAAAGAAGATCGCGTTCTTGACGTATCCGCAGCAGCGGC
CTTCAAAAAATAATTCCACAAGCAACTGTTCATATTTTTCCTGAAGTAGGCCAC
CTACCTATGGTAGAAATTCCTAGTGAAAGCGCTAAAGTTTATGAAGAGTTTTTGT
CCTCTATTAAATAAGAGCACATAATCATGACTGACTTATAAACAGCCAAGCATTT
AAAATGCTTGGCTGTTTATTTTAATGGCCAAATTATTCAACGACCAAGCTCTGCG
GTAAAATCGCAGTGGGTTTCTTGTTTTCATCAACAGCAACAAACGTGAAATACCC
CGTAATCGCATTTTTCTGATTATCAAAATACATACTTTCCACCAGCATATTAACTT
CAACTTTTAAACTCGTCCGCCCTACCTCTATAACACTGGCAGTCAATTCGACAATG
GTACCTGCGGGAACAGGATGCTTAAAATCGATTCGATCACTGCTGACGGTTACGA
TGCTTTGTCGAGAAAAACGAGTCGCTGCAATAAAAGAAACCTCATCCATCCACTG
CATTGCAGTGCCACCGAATAACGTATCATGATGATTTGTTGTCTCTGGAAATACC
GCTTTAGAAATAGTGGTTTTTGATACGCGCTTTCGCTGCGCAATAATATCTTCTCT
GCTAAGAGTTGCGGATGGCATACATAAACTCGCTTGATTAAGATTAATAATAAAT
AGTTAACAGTATATTGAACTGAGGGTCTGAAGAACTCTAATACCTCTGAAGAACT
TTGAGGCCGCTAGAGAGAAAAGACCAGTGATAATATTTCATCTTGCCATGAGAGC
TTATCATGAAAGCCTGTGCTTAAAATCAATCATTATATTTATTCATCTTTAATTGA
AATAATACCAATATATTTCATATATAATTTCACACTACCCTTATCTCACTAGACTT
CCCGCGCATAGGCGCAAACAATCAACGCAAGTTCACAATAAAGCGGTTCGCTGC
AACACATGCCCTAGCGTCTAAAGTAGCACGCACAACACTGGCCAGTCGTACTAGC
CCCTTTGCGATTCGTGCAGACGAGCAACAAGCGCTATTAAACTTACCTAAATTTC
TAACCACCACCATTGGTTCTTTTCCACAAACTCAAAAAACTCGTCAAATCCGCTTG
CAATTTAAACGCGATGACATAGATCTAATCGATTATCAAACCCGCATTCAAGCGC
TCATTAAAAACGCACCACTGGCAAGAAGTTCTACCTGCACTGACCAATATGCAAG
CGGCGGCGGAAGAGCTGCCTTTGATCGATCAAGAAGAAGGGAGCAGCAAAGAGG
AAAACAATCAAAAGAGGAGAGCAATCAAATAAAAACGAGTTATTGAGGATTTT
AATTTTAAAACAGGTATATTAATACCCTCTCTCGTAGTAAACAATGACTGTATTTA
CACAAAAATAAATAGAGGTATACCATGTCAAACATCTGGTTTGAAGTACCAAAG
ATTGAAGTATTAAACCGTCAAATGGAAAATACTGCCTGCAGCAACTTAGGCATTC
AAATTACAGAAATTGGCGATGATTATATCACTGGCACAATGCCAGCAGATGCACG
TACCTTCCAGCCAATGGGACTGATTCATGGCGGCTCAAATGTATTGCTGGCAGAA
ACACTGGGCAGCATGGCAGCTAACTGCTGTATTAATTTGTCTCAAGAATATTGTG

Figure 8 (continued):

TTGGCCAAGAAATTAACGCCAACCACATACGCGGTGTTCGTTCCGGCATAGTGAC
TGGCACAGCAACGCTAGTACACAAAGGAAGAACCTCCCAGATTTGGGAAATTCG
CATCGTTAAC*GATCCAAAGAATTCAAAAGCTTCTCGAGAGTACTTCTAGAGCGGCCG*
*CGGGCCCATCGATTTTCCACCCGGGTGGGGTACCAGGTAAGTGTACCCAATTCGCCCT*
*ATAGTGAGTCGTATTACAATTCACTGGCCGTCGTTTTAC*

Figure 9:

Amino acid sequence of the stabilized single ring mutant Glu460Ala/Ser462Ala/Val463Ala of Cpn60:

SEQ ID No 14: Cpn10 (nucleotides 458-751 of Figure 10):

MKIRPLHDRIVVRRKEEETATAGGIILPGAAAEKPNQGVVISVGTGRILDNGSVQALA
VNEGDVVVFGKYSGQNTIDIDGEELLILNESDIYGVLEA

SEQ ID No 15: Cpn60 (nucleotides 458-751 of Figure 10):

MAAKDVLFGDSARAKMLVGVNILADAVRVTLGPKGRNVVIEKSFGAPIITKDGVSV
AREIELKDKFENMGAQMVKEVASQANDQAGDGTTTATVLAQAIISEGLKSVAAGMN
PMDLKRGIDKATAAVVAAIKEQAQPCLDTKAIAQVGTISANADETVGRLIAEAMEKV
GKEGVITVEEGKGLEDELDVVEGMQFDRGYLSPYFINNQEKMTVEMENPLILLVDKK
IDNLQELLPILENVAKSGRPLLIVAEDVEGQALATLVVNNLRGTFKVAAVKAPGFGD
RRKAMLQDLAILTGGQVISEELGMSLETADPSSLGTASKVVIDKENTVIVDGAGTEAS
VNTRVDQIRAEIESSTSDYDIEKLQERVAKLAGGVAVIKVGAGSEMEMKEKKDRVD
DALHATRAAVEEGVVAGGGVALIRALSSVTVVGDNEDQNVGIALALRAMEAPIRQI
AGNAGAAGAAVVDKVKSGTGSFGFNASTGEYGDMIAMGILDPAKVTRSSLQAAASI
AGLMITTEAMVADAPVEEGAGGMPDMGGMGGMGGMPGMM

Figure 10:

SEQ ID No 16: DNA sequence of the stabilized single ring mutant
Glu460Ala/Ser462Ala/Val463Ala:

In the DNA sequence:
Small letters – the Cpn10-Cpn60 coding fragment,
Big bold letters = introduced mutations atcaaaaaatgcagcaaggacagattcctgcccaagaattagcagaaggtttcttgttagcactggccggcgctttattattaacgccgg
gttttgtcactgatgcgctgggttttacattactcgtccccgcgacgcgtaaagcgttggtccataaggtgattgcatttattacccctc
gcatgatgactgcaagcagctttcaagcgacgggtagttttcaggaaggctcgtttaaagatgtacattcgcacactgactcgcaaagca
gtcatgaaaaaatcacaattgaaggcgaatataccaaagacgataagtaggtatttttcggctagccgttgaaatcctagtaaaagccc
cgataaattaaccatctatttttcacagaggcaatttagcctttgtttaccttattgatcctaatacttgggatccaacagttggagagtctagc
aaatgaaaatccgtccattacatgatcgtattgttgttcgccgtaaagaagaagagaccgcaactgcgggtggtattatttttacc
gggcgctgcggcagaaaaaccaaatcaaggtgttgttatctctgtgggtactggccgtattcttgataatggttcagtgcaagcgctggc
ggttaacgaaggcgatgttgtcgttttggtaaatactcaggtcaaaatactatcgatatcgatggtgaagaattattgatttgaatga
aagtgatatctacggcgttttagaagcttaattattacactcacttttttatttaacctacaaaatttaaggaaagatcatggctgctaaagacg
tattatttggtgatagcgcacgcgcaaaaatgttggtaggtgtaaacattttagccgacgcagtaagagttaccttaggacctaa
aggtcgtaacgttgttatagaaaaatcatttggtgcaccgatcatcaccaaagatggtgtttctgttgcgcgtgaaatcgaattgaaagaca
aattcgaaaacatgggcgcacagatggtaaggaagttgcttctcaagccaacgaccaagccggtgacggcacaacgacagcgact
gtactagcacaggcgattatcagcgaaggcttgaaatctgttgcggctggcatgaatccaatggatcttaaacgtggtattgataaagcta
cggctgctgttgttgccgccattaaagaacaagctcagccttgcttggatacaaaagcaatcgctcaggtagggacaatctctgccaatg
ccgatgaaacggttggtcgtttaattgctgaagcgatggaaaaagtcggtaaagaaggtgtgattaccgttgaagaaggcaaaggcctt
gaagacgagcttgatgttgtagaaggcatgcagttcgatcgcggttacttgtctccgtacttcatcaacaaccaagaaaaaatgaccgta
gaaatggaaaatccattaattctattggttgataagaaaattgataaccttcaagagctgttgccaattcttgaaaacgtcgctaaatcaggt
cgtccattattgatcgttgctgaagatgttgaaggccaagcactagcaacattggtagtaaacaacttgcgcggcacattcaaggttgc
agcggttaaagcccctggttttggcgatcgtcgtaaagcgatgttgcaagatcttgccatcttgacgggtggtcaggttatttctgaagag
ctagggatgtctttagaaactgcggatccttcttctttgggtacggcaagcaaggttgttatcgataaagaaaacaccgtgattgttga
tggcgcaggtactgaagcaagcgttaatactcgtgttgaccagatccgtgctgaaatcgaaagctcgacttctgattacgacatcgaaaa
gttacaagaacgcgttgctaagcttgcgggcggcgttgccgtgattaaggttggtgcgggttctgaaatggaaatgaaagagaagaaa
gaccgtgttgacgatgcacttcatgcaactcgcgcagcggttgaagaaggtgttgttgcgggtggtggtgttgctttgattcgcgcactct
cttcagtaaccgtgttggtgataacgaagatcaaaacgtcggtattgcattggcacttcgtgcgatggaagctcctatccgtcaaatcgc

Figure 10 (continued):

gggtaacgcaggtgctgCagggGcagCggttgttgataaagtgaaatctggcacaggtagctttggttttaacgccagcacaggtg
agtatggcgatatgattgcgatgggtattttagaccctgcaaaagtcacgcgttcatctctacaagccgcggcgtctatcgcaggtttgat
gatcacaaccgaagccatggttgcggatgcgcctgttgaagaaggcgctggtggtatgcctgatatgggcggcatgggtggaatggg
cggtatgcctggcatgatgtaatcacttgtgattcattgtcctgatctgcttaccgtgtaaaaagatcaggctcaaggctgtctctataaaa
agccgtatctttgatgagtgttgtcttctgctgaaaacgacattcttggagtgcggctttttttgattttggtcataaaattcagaatattgtgta
attttatgtaactagctggcctataatgttgagttcctctgggtggcatgatctcatggtacttcacttaagcctgattcactgcg
gctttaacagtaaaataataacgcaacgtagaaacataataagcgtatggcattaatgaagacggctgcatttaattcagatc ically inactive. The
TRANSGENIC ORGANISMS WITH LOWER GROWTH TEMPERATURE

CROSS REFERENCE TO RELATED APPLICATIONS

Applicants claim priority under 35 U.S.C. §119 of European Application No. 03023032.0 filed Oct. 13, 2003. Applicants also claim priority under 35 U.S.C. §365 of PCT/EP2004/052492 filed Oct. 11, 2004. The international application under PCT article 21(2) was published in English.

The present invention in general relates to the growth temperature of organisms, especially plants and microorganisms and the manipulation of the tolerable cultivation temperature. More specifically, the present invention relates to the expression of heterologous proteins in microorganisms, and especially to the heterologous expression of heat sensitive proteins in bacteria, either gram-negative or gram-positive.

It is generally known that the mesophilic host *E. coli* is suitable for expression of a wide range of heterologous proteins, both intracellular and secreted. When expression of proteins is induced on a large scale in *E. coli*, problems are often encountered due to the production of intracellularly agglomerated protein, which is enzymatically inactive. The reason for the inactivity of these agglomerates, also called inclusion bodies, is the misfolding of the polypeptide chains which are intensely synthesized after induction or which cannot attain their natural active conformation when expressed in *E. coli* or other hosts. Various attempts for the in vitro folding of purified agglomerated protein have been proposed and are used on an industrial scale. However, the folding in vitro requires numerous processing steps to produce enzymatically active protein, i.e. protein in its correct folding structure. Feller, G. et al., Appl. Env. Microbiol, p. 1163-1165 (1999) describe the expression of the psychrophilic α-Amylase from the Antarctic psychrophile *Alteromonas haloplanktis* in *E. coli* by lowering the cultivation temperature of the transformed expression host to 18° C. It was demonstrated that the expression of active enzyme could be increased over that of the wild type *Alteromonas haloplanktis* and furthermore that the recombinantly produced enzyme had the same kinetic parameters as the wild type enzyme produced at 4° C. The authors therefore concluded that the psychrophilic enzyme is correctly folded when expressed recombinantly in *E. coli* at 18° C.

A drawback of low cultivation temperatures of mesophilic host organisms is the dramatically reduced growth rate, and, consequently a reduced synthesis rate of the heterologous protein.

In view of the known state of art the present invention aims at providing organisms, especially micro organisms which are capable of growth at lower temperature, for instance at temperatures similar to the range of growth temperatures of psychrophiles. Furthermore, the present invention aims at providing an expression system for heterologous proteins in micro organisms which are capable of producing correctly folded protein, i.e. protein with a structure which retains the enzymatic or interactive activity of the native wild type protein.

In a first aspect, the present invention provides a method for manipulation of cells and the resultant cells, characterized in that at least one gene from a psychrophilic micro organism coding for at least one chaperone or chaperonin is expressed. Such cells are selected among cultivated eukaryotic cells, i.e. anima and plant cells and entire plants, gram-negative and gram-positive bacteria, fungi and yeasts.

In a second aspect, the present invention provides a method for producing heterologous proteins in micro organisms as well as the micro organisms themselves, i.e. animal and plant cells, gram-negative and gram-positive bacteria, fungi and yeasts, characterized in that at least one gene from a psychrophilic micro organism coding for at least one chaperone or chaperonin is expressed. The heterologous proteins to be expressed comprise gene-products from mesophilic as well as psychrophilic organisms.

In a third aspect, there is provided a method for in vitro folding of aggregated or misfolded protein, characterized in that at least one chaperone or chaperonin from a psychrophilic micro-organism is contacted with the aggregated or misfolded protein in presence of necessary nucleotides.

In a fourth aspect, DNA and amino acid sequences are provided for native chaperonins Cpn10 and Cpn60 of *Oleispira antarctica* along with mutant chaperonins with altered characteristics as well as methodology and guidelines for cloning, expressing and adapting chaperones for enhancing the expression of heterologous proteins, and especially thermo-sensitive heterologous proteins, in their native conformation in host organisms, for adapting host organisms to lower growth temperatures and for re-folding, at low thermal conditions, denatured protein in vitro.

The invention is illustrated in relation to the chaperones from the psychrophilic bacterium *Oleispira antarctica*, which have been designated Cpn60 and Cpn10 and which are co-operative in their wild type forms.

The standard growth temperature of the widely used expression host bacterium *E. coli* is 37° C. with an experimental lower limit of approximately 15° C. The theoretical lower limit can be calculated to 7.5° C. by the square-root growth model of Ratkowsky et al., 3. Bacteriol., 1222-1226 (1983).

It has now been discovered that the expression of chaperonin Cpn60 and its co-operating co-chaperonin Cpn10 in *E. coli* decreases the actual growth temperature to 0 to 7° C. with a theoretical minimum of −13.7° C. The growth rate of these coldness-adapted *E. coli* reaches 0.28/h at 8° C. and 0.22/h at 4° C.

When heterologous genes are expressed in *E. coli* which harbour both the chaperonin Cpn60 and its co-chaperonin Cpn10, then the expression can take place at significantly lower cultivation temperatures, i.e. 0 to 7° C. and thermo-sensitive protein can be produced by *E. coli* in its native conformation, e.g. enzymatically active.

It was shown that Cpn60 adapts its tertiary structure in a temperature-dependent manner. At the normal growth temperature of *O. antarctica* of 4 to 10° C., the predominant tertiary structure of Cpn60 is a heptameric single ring of identical subunits along with lower molecular weight dissociation intermediates. In a temperature range of 12 to 24° C., Cpn60 is predominantly present as a 14-mer, consisting of two stacked rings, each comprised of seven identical subunits. However, the dissociation of the stacked heptameric rings at lower temperature is dependent on the presence of nucleotides of adenine, citidine, uridine or guanidine. It was shown that the activity of Cpn60 to refold denatured proteins is dependent on nucleotides, e.g. adenonsine triphosphate (ATP).

From the following examples, analytical data of the chaperonins Cpn60 and Cpn10 of *Oleispira antarctica* will be apparent. As a consequence, the skilled persons will be enabled to identify and clone homologous genes encoding chaperones from either *Oleispira antarctica* itself or from other psychrophilic microorganisms, e.g. other eubacteria or archaeobacteria using the sequence information given for the chaperonins of *O. antarctica* and the cloning strategy below or other known procedures. As source organisms for chaperones with similar functional properties as and/or homology to those specifically disclosed herein, the following can be used: *Moraxella, Alteromonas haloplanktis*.

Homologous chaperones, derivatives or mutant forms of the chaperonins Cpn60 and Cpn10 of *Oleispira antarctica* which retain the functional properties in respect of the lowering of the growth temperature of a transformed mesophilic host organism and/or in respect of the chaperone activity to refold denatured proteins extracellularly, for example in vitro, are also accessible on the basis of the examples given below.

When screening other psychrophilic organisms for chaperonins homologous to those of *O. antarctica*, sequence alignment studies and comparisons can be employed, for example exploiting homologies of Cpn60 of *O. antarctica* to GroEL of *E. coli* and Cpn60 of *Paracoccus denitrificans* in order to identify residues with an influence on substrate specificity and/or conformation of the chaperonin. Variants can be constructed in accordance with the methodology presented below for producing mutant chaperonins of *O. antarctica*.

Derivatives or mutant forms of *O. antarctica* can readily be obtained by genetically engineering the DNA sequence of the genes encoding Cpn60 and/or Cpn10. Such mutants may have altered substrate binding specificities, altered nucleotide binding properties or an altered secondary or tertiary structure or altered interaction parameters of a chaperonin with its co-chaperonin, e.g. of mutant Cpn60 with mutant Cpn10. It can be expected that mutations introduced at sites responsible for substrate binding change the substrate specificity, mutations at sites responsible for the association of subunits to the single ring conformation change the single ring structure, and mutations at sites responsible for the interaction of ring structures with one another to stacked rings change the conformation and consequently the stability and the temperature-dependent association of rings and ultimately their activity and/or substrate specificity.

SHORT DESCRIPTION OF THE FIGURES

FIG. 1 shows the amino acid sequences of native Cpn10 (SEQ ID No 1) and Cpn60 (SEQ ID No 2) of *O. antarctica*.

FIG. 2 shows the DNA sequences of native Cpn10 and Cpn60 (SEQ ID No 3) of *O. antarctica*.

FIG. 3 shows the amino acid sequence of esterase (SEQ ID No 4) of *O. antarctica*

FIG. 4 shows the DNA sequence of esterase (SEQ ID No 5) of *O. antarctica*.

FIG. 5 shows the amino acid sequences of native Cpn10 (SEQ ID No 6) and Cpn60 (SEQ ID No 7) of *O. antarctica* and esterase (SEQ ID No 8) of *O. antarctica*.

FIG. 6 shows the DNA sequence of the expression cassette of native Cpn10 and Cpn60 and of *O. antarctica* with the esterase (SEQ ID No 9) of *O. antarctica*.

FIG. 7 shows the amino acid sequences expressed from the expression vector coding for the co-expression of native Cpn10 (SEQ ID NO: 10) and the stabilized single ring mutant Glu460Ala/Ser462Ala/Val463Ala of Cpn60 (SEQ ID NO: 11) of *O. antarctica* with the esterase (SEQ ID NO: 12) of *O. antarctica*.

FIG. 8 shows the DNA sequence of the expression vector SEQ ID No 13) coding for the co-expression of native Cpn10 (SEQ ID No 10) and the stabilized single ring mutant Cpn6O (SEQ ID No 11) of *O. antarctica* with the esterase (SEQ ID No 12) of *O. antarctica*.

FIG. 9 shows the amino acid sequences of native Cpn10 (SEQ ID NO: 14) and of the stabilized single ring mutant Glu460Ala/Ser462Ala/Val463Alaof Cpn60 (SEQ ID NO: 15) of *O. antarctica*.

FIG. 10 shows the DNA sequence of the stabilized single ring mutant Glu460Ala/Ser462Ala/Val463Ala of Cpn60 (SEQ ID NO: 16) of *O. antarctica*.

The examples below describe the methodology of cloning the chaperonin genes Cpn60 and Cpn10 from *O. antarctica* as well as generating mutant and variant chaperones. Therefore, the skilled person will be instructed on how to influence stability and activity parameters of chaperones having similar functional parameters as those described specifically.

EXAMPLE 1

Cultivation of *Oleispira antarctica* and Isolation of Cn60 and Cpn10

*O. antarcitca* RD-8 were cultivated at 4° C. in 400 mL ONR7a medium (Dyksterhouse et al., I. J. Sys. Bacteriol. 116-123 (1995)) supplemented with 0.2 vol % Tween 80 (Sigma Chemicals) to an optical density of 0.7 to 0.8 at 600 nm, harvested by centrifugation (4500×g, 30 min, 4 IC) and frozen at −20° C. Thawed cells were suspended in two-fold volume of buffer containing 50 mM Tris-HCl, pH 7.0, 10 mM $MgCl_2$, 10 mM KCl, 2 M EDTA, 1 mM DTT, I tablet protease inhibitor cocktail (Roche) and Dnase I grade II, then homogenized in a French press at 68.95 bar (1000 psi), centrifuged (35,000×g, 35 min, 4° C.) and the supernatant concentrated by ultrafiltration by centrifugation against a membrane with a cut-off at 10 kDa (Centricon, Amicon Inc.) to 2 mL.

The purification was by elution from a Mono-Q HR 10/10 ion exchange column, equilibrated with 50 mM Tris-HCl, pH 7.0, 10 mM $MgCl_2$, 10 mM KCl, with a 0-1 M NaCl gradient in the same buffer for 200 min at 2.0 mL/min. Fractions containing Cpn60 and Cpn10 were identified by SDS-PAGE with subsequent blotting and immunodetection with a polyclonal antibody directed against the N-termini of both Cpn10 and Cpn60 as well as by an activity test of the refolding activity using chemically denatured rhodanese as the substrate. Active fractions were eluted at 0.30-0.45 M NaCl, pooled, dialyzed against 50 mM Tris-HCl, pH 7.0, 10 mM $MgCl_2$, 10 mM KCl, 150 mM NaCl and concentrated by centrifugation against a membrane with a cut-off at 10 kDa (Centricon, Amicon Inc.). The concentrated pooled fractions were purified by gel-filtration on a Superdex 200 16/60 column, equilibrated in 50 mM Tris-HCl, pH 7.0, 10 mM $MgCl_2$, 10 mM KCl, 150 mM NaCl at 4° C. at a flow-rate of 1 mL/min. Fractions were pooled, dialyzed against 50 mM Tris-HCl, pH 7.0, 10 mM $MgCl_2$, 10 mM KCl, concentrated by ultrafiltration by centrifugation (10 kD cut-off membrane), then further purified by ion-exchange chromatography on a Mono-Q HR 5/5 column at 0.5 mL/min of a linear gradient (20 mL) of 0-1 M NaCl and fractions pooled.

EXAMPLE 2

Cloning and Characterization of Chaperonin Cpn60 and Cpn10 of *Oleispira antarctica*

Starting from *Oleispira antarctica* RB-8, available as DSMZ accession No 14852, a comprehensive genomic library comprising 5×10⁸ phage particles/µL, total of 8 mL with an average insert size of 7.5 kb was created using the ZAP Express Kit of Stratagene according to the manufacturers instructions. Briefly 7.5 kb fragments of genomic DNA from *O. antarctica* were cloned into a plasmid using the well known procedure of the ZAP Express kit (Stratagene).

Degenerate forward primer 5'-GCI GCI GGI ATG AAY CCI ATG G (Seq ID No 17) and reverse primer 5'-CCI CCI CCI GCI ACI ACI CCY TC (Seq ID No 18) were designed on the basis of the sequences analyzed from purified chaperonin fragments SVAAGMNPMDLQR (Seq ID No 19) and VEEGVVAGGGVAAL-LR (Seq ID No 20), respectively. These primers were used for PCR amplification of the genomic DNA of strain RB-8 (Smits et al., *Environ. Mircrobiol.* 307-317 (1999)). The amplified fragment of approximately 930 bp was cloned into plasmid pCR2.1 (Invitrogen). Briefly, the fragment was purified from an agarose gel and ligated into the pCR2.1 plasmid. Subsequent sequencing of the cloned PCR product revealed a high similarity of its deducible amino acid sequence to the Cpn60/Hsp60 family.

The cloned PCR fragment was then excised from vector pCR2.1, labelled with digoxygenin (DIG DNA Labelling Kit, Roche Diagnostics) and used as a hybridisation probe to screen the lambda phage genomic library of RB-8. From phage plaques that hybridized and identified using the immuno-detection of digoxygenin (Roche Diagnostics), the cloned DNA fragments were rescued with the infection of helper phage f1 to give plasmids pBK-CMV. The inserted DNA fragments of pBK-CMV was sequenced. The amino acid sequence of Cpn60 and Cpn10 translated from the DNA sequence (shown in FIG. 2) are given below in FIG. 1.

EXAMPLE 3

Simultaneous Expression of Cpn60 and Cpn10 of *Oleispira antarctica* in *E. coli*

The expression of Cpn60 and Cpn10 was induced from the vector pPST26, originating from the lambda clone No 26 that hybridized with the DNA probe for cpn60, designated pBK26, which was deleted upstream by a restriction with PstI. The expression vector carries both genes in the orientation that enables their expression from the $P_{lac}$-promoter. For overexpression, *E. coli* cells XL-1 Blue MRF were transformed with pPST26, grown in LB medium to an optical density at 600 nm of 0.6 to 0.8 and induced by the addition of IPTG (isopropyl-β-D-thiogalactopyranoside) to a final concentration of 2 mM. Cells were harvested by centrifugation 2 to 3 hours after induction, resuspended in 2 mM EDTA, 1 mM dithiothreitol (DTT), 1 tablet protease inhibitor cocktail (Roche) and Dtase I grade II, incubated on ice for 30-45 min and sonicated for 4 min total time. The cell lysate was centrifuged at 10,000×g, 30 min, 4° C. and the soluble supernatant was dialyzed overnight against 50 mM Tris-HCl, pH 7.0, 10 mM $MgCl_2$, 10 mM KCl, then concentrated by ultrafiltration by centrifugation against a membrane with a cut-off at 10 kDa (Centricon, Amicon Inc.) to 2 mL.

EXAMPLE 4

Mutants of Cpn60 with Increased Stability of the Tetradecameric Structure

Mutants of Cpn60 were constructed which show an increased stability of the two stacked heptameric ring conformations, forming the tetradecamer of Cpn60. Mutations were introduced by site-directed mutagenesis using primers in PCR amplifications which carry the desired nucleotide exchanges to yield a different codon, as it is generally known to the skilled person. For introducing the mutations into the wild type gene of Cpn60 from *O. antarctica*, the following oligonucleotides were used in PCR:

Lys468Thr: 5'-GGT GGT CAG TGG TTG TTG TTG ATA CAG TGA AAT CTG GCA CAG-3' (Seq ID No 21) and 5'-CCT GTG CCA GAT TTC ACT GTA TCA ACA ACC ACT GAC C-3' (Seq ED No 22)

Ser471Gly: 5'-GGT GAT AAA GTG AAA GGT GGC ACA GGT AGC-3' (Seq ID No 23) and 5'-GCT ACC TGT GCC ACC TrT CAC TTT ATC AAC-3' (Seq ID No 24)

Lys471Thr-5'-GGT CAG TGG TTG TTG ATA CAG TGA AAG GTG GCA CAG GTA GCT TTG G-3' (Seq ID No 25) and 5'-CCA AAG CTA CCT GTG CCA CCT TTC ACT GTA TCA ACA ACC ACT GAC C-3' (Seq ID No 26)

Glu460Ala/Ser462Ala/Val463Ala. 5'-CCT AAC GCA GGT GCT GCA GGG GCA GCG GTT GTT GAT AAA GTG-3' (SEQ ID NO: 27)and 5'-CTC TTT ATC AAC AAC CGC TGC CCC TGC AGC ACC TGC GTT ACC-3' (SEQ ID NO: 28).

Firstly, Lysin 468 was exchanged for a Threonin, and secondly, Serin 471 was exchanged for a Glycine and thirdly, a double mutant Lys468Thr/Ser471Gly was produced These plasmids were expressed in *E. coli* strain XLOLR as described in Example 3 with the appropriate antibiotic kanamycin added. All three mutants demonstrated a more stable association of the heptameric rings to the tetradecameric stacked ring structure during native gel elechrophoresis (7.5% PAGE, poly acryl amide gel electrophoresis according to Laemmli).

EXAMPLE 5

Mutant of Cpn60 with Decreased Stability of the Tetradecameric Structure

As a fourth variant, a mutant with three amino acid substitutions was produced as above, introducing the mutations Glu460Ala/Ser462Ala/Val463Ala. This mutant was shown in native PAGE to have a single ring heptameric conformation with an apparent mass of approximately 400 kDa, which corresponds to the wild-type single heptameric ring conformation The above described mutants were purified as described in Example 1. The analysis of the mutant proteins by circular dichroism demonstrated that the triple mutant Glu460Ala/Ser462Ala/Val463Ala as well as the double mutant Lys468Thr/Ser471Gly were not destabilized in their respective overall secondary conformations in comparison to the wild-type Cpn60.

Using the measurement of peptide ellipticity at 220 nm to monitor the loss of secondary structure due to increasing temperature, it could be demonstrated that the stabilized double ring mutant Lys468Thr/Ser471Gly has an increased temperature stability at 45-55° C. and a at a rate for ATP hydrolysis 1.3 to 1.6 times higher than the wild type and the stabilized single ring mutant Glu460Ala/Ser462Ala/Val463Ala, the latter having temperature stability up to 24-28° C.

Similar results for an increased temperature stability at increased hydrolysis rates for ATP are obtained for mutants of Cpn60 of *O. antarctica* Leu468Thr and Ser471Gly, which each show an increased stability of the double ring structure compared to the wild type, at least in presence of ATP.

With a view to adapting chaperones to the cultivation temperature, it can therefore be concluded that single ring variants of chaperonins, especially of Cpn60 of *O. antarctica* RB-8, are essential for producing protein in its correct conformation at low temperatures, e.g. at 0-8° C., whereas variants of chaperoning, especially of Cpn60 of *O. antarctica* RB-8, are essential for producing protein in its correct conformation at higher temperatures, e.g. at above 10-12° C.

EXAMPLE 6

Chaperone Activity of Cpn60 and its Mutants in vitro

The wild type Cpn60 from *O. antarctica*, without its co-chaperonin Cpn10 has refolding activity under both physiological and temperature stress conditions of 0-30° C., which is in correlation with the range of the growth temperature of the source organism.

When used in in vitro folding procedures, isolated wild type Cpn60 refolds denatured protein as a single ring at 4 to 8° C., whereas at >12° C., the predominant conformation of the active form is the double ring complex.

When using chemically denatured mtMDH (mitochondrial malate dehydrogenase) (Nielsen et al., Mol. Cell. 93-99 (1995)) as the substrate for in vitro refolding procedures, it was found that spontaneous refolding occurred at about 16-24% at a temperature range of 4 to 30° C. in 50 mM Tris-HCl, pH 7.0, 50 mM $MgCl_2$, 50 mM KCl.

When testing the refolding activity of the wild type Cpn60, the stabilized single ring mutant Glu460Ala/Ser462Ala/Val463Ala, and the stabilized double ring mutant Lys468Thr/Ser471Gly under the same conditions with added Cpn10 and ATP (1 mM), it was found that the stabilized single ring mutant catalysed refolding at 4 to 8° C. at 70-80%, but was inactive for refolding at above 10° C. The behaviour of the stabilized single ring mutant led to the conclusion that at the low temperature, the co-chaperonin Cpn10 could bind even to the heptameric conformation, whereas at elevated temperature presumably Cpn10 could not be released from this heptameric single ring.

In contrast to the stabilized single ring mutant, the stabilized double ring mutant Lys468Thr/Ser471Gly yields a low refolding effect (20%) at low temperature of 4° C., approximately four times lower than the stabilized single ring mutant (80%).

Wild type Cpn60 was active from 4 to 20° C., showing a higher refolding activity at lower temperatures.

Although the wild type Cpn60 as well as the stabilized single ring mutant could not catalyse refolding at temperatures of above 25-30° C., the stabilized double ring mutant was active, i.e. at 28° C. the refolding yield was more than ten times that of the wild type Cpn60 and that of the stabilized single ring mutant, with activity up to 36° C.

From these results it can be inferred that the temperature range, in which a chaperonin is active for refolding denatured protein can be influenced by its conformation as a stabilized single or stabilized double ring variant. Furthermore, at least the amino acids in homologous positions as Lys468 and Ser 471, respectively, in Cpn60 of *O. antarctica* are responsible for this temperature range of chaperone activity.

Furthermore it is demonstrated that even as a single ring structure, Cpn60 catalyzes the refolding of denatured protein when in combination with its co-chaperonin. Further experiments using a competition assay of radio-labelled Cpn10 and non-labelled Cpn10 at 4° C. and 20° C. demonstrated that the co-chaperonin is released from the stabilized single ring mutant of Cpn60 only at the lower temperature and in presence of denatured protein substrate (denatured mtMDH). At the higher temperature, the bound co-chaperonin was not released from this mutant Cpn60 when denatured protein substrate was added. When testing the stabilized double ring mutant of Cpn60 under the same conditions, the release of the co-chaperonin was independent from the temperature and lower by a factor of 4-5 compared to the stabilized single ring mutant.

EXAMPLE 7

Influence of Variant Chaperones on the Growth of Transformed Host Organisms

The effect of the presence of a gene product coding for the wild type chaperone from a psychrophilic organism as well as of variant chaperones thereof have been assessed for the growth of *E. coli* at varying temperatures. *E. coli* have been transformed with a plasmid bearing, under the control of an IPTG inducible lac promoter the gene for wild type chaperonin Cpn60 and its co-chaperonin Cpn10 of *O. antarctica*, the stabilized single ring mutant Glu460Ala/Ser462Ala/Val463Ala, and the stabilized double ring mutant Lys468Thr/Ser471Gly, respectively. As shown in FIG. 9, *E. coli* without heterologous chaperone grew at 15° C. only to some extent ($OD_{600}$ after 48 h incubation 0.74+/−0.24), at 4° C., no growth was observed. Only *E. coli* expressing the wild type chaperonin Cpn60 and Cpn10 or the stabilized single ring mutant Glu460Ala/Ser462Ala/Val463Ala grew at 4° C. up to an $OD_{600}$=1.5+/−0.14 after 48 h. However, at 15° C., the stabilized single ring mutant Glu460Ala/Ser462Ala/Val463Ala ($OD_{600}$=0.75 +/−0.10) did not enhance viability, but wild type Cpn60 and Cpn10 ($OD_{600}$=1.45 +/−0.12) and the stabilized double ring mutant Lys468Thr/Ser471Gly ($OD_{600}$=1.63 +/31 0.24) allowed for an enhanced growth.

From these findings it is clear that when screening for or constructing variant chaperonins it has to be considered that at lower temperatures for growth of host cells and for refolding of denatured protein to their native conformation the effectiveness, i.e. activity of the chaperonin is dependent on its tertiary conformation. As has been detailed for chaperonin Cpn60 and Cpn10 of *O. antarctica*, the active conformation of Cpn60 at low temperatures, I.e. below 12° C. is the single heptameric ring structure, whereas at higher temperatures, i.e. above 12° C., the active conformation of Cpn60 is the double ring structure.

Since this temperature dependence of the chaperonin activity has been elucidated for Cpn60 of *O. antarctica*, the skilled persons will be able to apply these findings to homologous chaperones from psychrophiles and to mutant and variant forms thereof using standard methodology. In detail, the influence of the amino acids Lys468 and Ser471 on the stabilisation of the association of the heptameric rings of Cpn60 has been demonstrated. Accordingly, the influence on stability of the tertiary conformation of their functionally equivalent residues in homologous chaperonins is evident and can be used to manipulate the tertiary structure and, as a consequence the temperature dependence of homologous and variant chaperones.

As one mutant form of a homologous chaperonin, the GxoEL from *E. coli* was mutated doubly by Thr468Lys and Gly471 Ser to arrive at a chaperonin with altered activity at temperatures below that of unmodified GroEL. The sequence of GroEL of *E. coli* is available as accession No P06139 at the Swissprot databank.

EXAMPLE 8

Chaperone Activity of Cpn60 and its Mutants in vivo

The influence of chaperones from psychrophilic organisms on the expression of protein in its native, i.e. non-denatured conformation is demonstrated on the example of the temperature sensitive esterase from *O. antarctica* in *E. coli* with and without presence of the heterologous chaperonin Cpn60 from *O. antarctica*.

The esterase gene from *O. antarctica* RB-8 (DSMZ No. 14852T) was cloned from the genomic lambda library described in example 2. Detection of clones expressing active esterase was after infection of *E. coli* XL1-Blue MRF' and incubation by overlay with an aqueous solution containing per mL 60 µL naphthyl acetate (20 mg/mL acetone), 0.25 mM IPTG and 16 µL of Fast Blue RR (80 mg/mL dimethyl sulfoxide). Positive clones exhibited a brown halo after about 2 h incubation and were isolated after consequent phage particle dilution, infection of *E. coli* and halo detection. The inserted DNA sequence from positive clones was rescued by helper phage infection and sequenced. The amino acid sequence and the DNA sequence of the esterase from *O. antarctica* are given in FIGS. 3 and 4, respectively.

For expression experiments of the thermo sensitive esterase as cloned above, the esterase gene (est) was cloned into an *E. coli* expression vector under the control of a lac-promoter, alternatively in combination with an expression cassette under a lac-promoter of the wild type chaperonin Cpn60 and its co-chaperonin Cpn10 (cpn10::cpn60::est, see FIGS. 5 and 6 for amino acid and DNA sequences, respectively) and in combination with the stabilized single ring mutant Glu460Ala/Ser462Ala/Val463Ala and Cpn10 (cpn10::stabilized single ring mutant Glu460Ala/Ser462Ala/Val463Ala ::est, see FIGS. 7 and 8 for amino acid and DNA sequences, respectively), under control from a lac-promoter as well. Standard PCR-cloning procedures with primers designed according to the established gene sequences were used. *E. coli* cells TOP10 (Invitrogen) were transformed with the above plasmids by electroporation and incubated in LB broth containing the appropriate antibiotic kanamycin at 4, 8, 10, 15, 20, 30, and 37° C. each. Induction was done with 1 mM IPTG. Once the cultures reached maximal esterase activities, the cells were harvested by centrifugation, resuspended in 50 mM Tris-HCl, pH 7.0, 50 mM MgCl$_2$, 50 mM KCl containing one protease inhibitor tablet (Roche Diagnostics) and Dnase I grade II, incubated on ice for 30-45 min and sonicated for a total of 4 min. After centrifugation at 10,000×g for 30 ruin at 30, the supernatant was dialysed overnight against 50 mM Tris-HCl, pH 7.0, 50 mM MgCl$_2$, 50 mM KCl and concentrated by ultrafiltration with a 10 kDa cut-off membrane (Centricon, Millipore).

Purification was by ion-exchange chromatography on Mono-Q HR 10/10, equilibrated with 50 mM Tris-HCl, pH 7.0, 50 mM MgCl$_2$, 50 mM KCl, elution with a 0-1 M NaCl gradient in the same buffer for 200 min at 0.5 mL/min. Esterase containing fractions were eluted at about 0.3 M NaCl and pooled. After changing the buffer by dialysis and ultrafiltration, the pool was loaded onto a Resource 15PHE hydrophobic chromatography column, previously equilibrated with 50 mM Tris-HCl, pH 7.0, 1 M (N$_4$)$_2$SO$_4$, washed with a decreasing 1.0-0 linear (NH$_4$)$_2$SO$_4$ gradient in 10 mM Tris-HCl, pH 7.0. The fractions active for esterase were pooled, dialysed against 10 mM Tris-HCl, pH7.0, 150 mM NaCl and concentrated as before. Finally, gel filtration was performed on a Superose 12 ER 10/30 in 10 mM Tris-HCl, pH 7.0, 150 mM NaCl at 4° C. and 0.4 mL/min N-terminal sequencing was employed to corroborate the identity of the enzyme.

The results are given in table 1 below.

TABLE 1

| Growth temperature [° C.] | Without additional chaperonin | | cpn10::cpn60::est | | cpn10::stabilized single ring mutant Glu460Ala/Ser462Ala/Val 463Ala::est | |
|---|---|---|---|---|---|---|
| | Protein expression[1] | Esterase activity[2] | Protein expression[1] | Esterase activity[2] | Protein expression[1] | Esterase activity[2] |
| 37 | 2-5 | 12 | 2-5 | 12 | 2-5 | 12 |
| 30 | 2-5 | 127 | 2-5 | 127 | 2-5 | 127 |
| 20 | <2 | 504 | 2-5 | 768 | <2 | 528 |
| 15 | <1 | 1560[3] | 2-5 | 2040[4] | <1 | 1400[3] |
| 10 | n.d. | n.d. | 2-5 | 2304[5] | 2-5 | 2304[6] |
| 8 | n.d. | n.d. | 2-5 | 2400[5] | 2-5 | 2400[6] |
| 4 | n.d. | n.d. | 2-5 | 2400[5] | 2-5 | 2400[6] |

[1]Expression as % by weight of total cell protein
[2]Whole cell activity in µmol tributyrin per min per g cell lyophilisate, measured in Tris-HCl buffer, pH 8.5 at 20° C.
[3]Growth rate of 0.15/h, late-exponential phase reached in 60 h
[4]Growth rate of 0.46/h, late-exponential phase reached in 24 h
[5]Growth rate of 0.22-0.28/h, late-exponential phase reached in 30 h
[6]Growth rate of 0.5/h, late-exponential phase reached in 20 h
n.d. No growth observed or growth rate below 0.01/h When analysing the heterologously expressed cloned esterase from *O. antarctica* in *E. coli* under identical conditions except for the presence of IPTG inducible chaperonin genes it was found that without additional chaperonins in *E. coli*, at 37° C. the hydrolytic activity was very low, i.e. 190 µmol/min/g. When reducing the cultivation temperature, higher specific activity of the esterase was observed. However, the higher specific activity correlated with a dramatically reduced expression level at lower temperatures.

In *E. coli* also expressing the chaperonin from *O. antarctica* in its wild type and stabilized single ring mutant forms, respectively, esterase was expressed at much higher level, with the wild type chaperonin reaching the late-exponential growth phase after 30 h and the stabilized single ring mutant chaperoning after only 20 h.

When comparing the different chaperonins expressed, it becomes clear that their structure greatly influences their activity at different temperatures. In detail, the stabilized single ring mutant Glu460Ala/Ser462Ala/Val463Ala was only efficient for production of active esterase at below 10° C.

At temperatures above 20° C., the esterase activity was significantly lower for all transformants and it is assumed that this is due to the instability of the esterase at these temperatures. However, when analysing the fluorescence intensity of esterase obtained from cultures at 4° C. and 37° C. for both chaperonin transformants, i.e. wild type cpn10::cpn60::est and cpn10::stabilized single ring mutant Glu460Ala/Ser462Ala/Val463Ala::est, the fluorescence intensity of esterase for each transformant measured for the 4° C. culture were five times higher than those for the 37° C. culture. Therefore, misfolding of the thermo-sensitive esterase due to its expression at 37° C. can practically ruled out but higher fluorescence values for the esterase expressed at 4° C. indicate a better folding state, correlating with a higher specific esterase activity.

The invention claimed is:

1. A process for producing a protein by heterologous expression in a host cell wherein said host cell is selected from a group comprising Gram-positive or Gram-negative bacteria, wherein said host cell contains a gene sequence encoding said heterologous protein, wherein said host cell is cultivated at a temperature of below 25° C. and wherein said host cell expresses a DNA sequence encoding a chaperonin selected from a group consisting of Cpn60 according to SEQ ID NO: 2, a stabilized single ring mutant chaperonin of SEQ ID NO: 11, and a stabilized double ring mutant of Cpn60 according to SEQ ID NO: 2 with the mutation of Lys468Thr and Ser471Gly.

2. The process of claim 1, wherein the host cell is further contains a DNA sequence encoding a chaperonin Cpn10 according to SEQ ID NO: 1.

3. The process of claim 1, wherein the heterologous protein is selected from the group consisting of mammalian proteins, bacterial proteins, fungal proteins or yeast proteins, and mutants or fusions thereof.

4. The process of claim 1, wherein the heterologous protein has enzymatic activity or hormonal activity in its native conformation.

5. The process of claim 1, wherein the cultivation temperature is 4 to 15° C.

6. The process of claim 2, wherein the heterologous protein has enzymatic activity or hormonal activity in its native conformation.

7. The process of claim 2, wherein the cultivation temperature is 4 to 15° C.

8. The process of claim 3, wherein the bacterial proteins are mesophilic bacterial proteins.

* * * * *

UNITED STATES PATENT AND TRADEMARK OFFICE
CERTIFICATE OF CORRECTION

| | | |
|---|---|---|
| PATENT NO. | : 7,811,784 B2 | Page 1 of 1 |
| APPLICATION NO. | : 10/575505 | |
| DATED | : October 12, 2010 | |
| INVENTOR(S) | : Ferrer et al. | |

It is certified that error appears in the above-identified patent and that said Letters Patent is hereby corrected as shown below:

| | |
|---|---|
| Col. 5, line 47 | Delete "Dtase I" and insert --(Dnase I)-- in its place. |
| Col. 6, line 10 | Delete "Lys471 Thr-5'-" and insert --Lys471 Thr: 5'- -- in its place. |
| Col. 6, line 14 | Delete "/Val463Ala." and insert --/Val463Ala:-- in its place. |
| Col. 6, line 19 | Delete "Lysin 468" and insert --Lysine 468-- in its place. |
| Col. 6, line 19 | Delete "Threonin" and insert --Threonine-- in its place. |
| Col. 6, line 20 | Delete "Serin" and insert --Serine-- in its place. |
| Col. 6, line 53 | Delete "C. and a at a rate" and insert --C., and a rate-- in its place. |
| Col. 7, line 1 | Delete "chaperoning" and insert --chaperonins-- in its place. |
| Col. 8, line 38 | Delete "Le" and insert --i.e.-- in its place. |
| Col. 8, line 57 | Delete "GxoEL" and insert --GroEL-- in its place. |
| Col. 10, line 2 | Delete "30 ruin" and insert --30 min-- in its place. |
| Col. 10, line 17 | Delete "pH7.0," and insert --pH 7.0,-- in its place. |
| Col. 53, line 30, Claim 1 | After "25°C" and before "and", please delete the ".". |

Signed and Sealed this
Twelfth Day of April, 2011

David J. Kappos
*Director of the United States Patent and Trademark Office*

SEQUENCE LISTING

<160> NUMBER OF SEQ ID NOS: 28

<210> SEQ ID NO 1
<211> LENGTH: 97
<212> TYPE: PRT
<213> ORGANISM: artificial sequence
<220> FEATURE:
<223> OTHER INFORMATION: Cpn10 of Oleispira antarctica

<400> SEQUENCE: 1

```
Met Lys Ile Arg Pro Leu His Asp Arg Ile Val Arg Arg Lys Glu
1               5                   10                  15

Glu Glu Thr Ala Thr Ala Gly Gly Ile Ile Leu Pro Gly Ala Ala
                20                  25                  30

Glu Lys Pro Asn Gln Gly Val Val Ile Ser Val Gly Thr Gly Arg Ile
            35                  40                  45

Leu Asp Asn Gly Ser Val Gln Ala Leu Ala Val Asn Glu Gly Asp Val
        50                  55                  60

Val Val Phe Gly Lys Tyr Ser Gly Gln Asn Thr Ile Asp Ile Asp Gly
65                  70                  75                  80

Glu Glu Leu Leu Ile Leu Asn Glu Ser Asp Ile Tyr Gly Val Leu Glu
                85                  90                  95

Ala
```

<210> SEQ ID NO 2
<211> LENGTH: 548
<212> TYPE: PRT
<213> ORGANISM: artificial sequence
<220> FEATURE:
<223> OTHER INFORMATION: Cpn60 of Oleispira antarctica

<400> SEQUENCE: 2

```
Met Ala Ala Lys Asp Val Leu Phe Gly Asp Ser Ala Arg Ala Lys Met
1               5                   10                  15

Leu Val Gly Val Asn Ile Leu Ala Asp Ala Val Arg Val Thr Leu Gly
                20                  25                  30

Pro Lys Gly Arg Asn Val Val Ile Glu Lys Ser Phe Gly Ala Pro Ile
            35                  40                  45

Ile Thr Lys Asp Gly Val Ser Val Ala Arg Glu Ile Glu Leu Lys Asp
        50                  55                  60

Lys Phe Glu Asn Met Gly Ala Gln Met Val Lys Glu Val Ala Ser Gln
65                  70                  75                  80

Ala Asn Asp Gln Ala Gly Asp Gly Thr Thr Thr Ala Thr Val Leu Ala
                85                  90                  95

Gln Ala Ile Ile Ser Glu Gly Leu Lys Ser Val Ala Ala Gly Met Asn
            100                 105                 110

Pro Met Asp Leu Lys Arg Gly Ile Asp Lys Ala Thr Ala Ala Val Val
            115                 120                 125
```

-continued

```
Ala Ala Ile Lys Glu Gln Ala Gln Pro Cys Leu Asp Thr Lys Ala Ile
    130                 135                 140

Ala Gln Val Gly Thr Ile Ser Ala Asn Ala Asp Glu Thr Val Gly Arg
145                 150                 155                 160

Leu Ile Ala Glu Ala Met Glu Lys Val Gly Lys Glu Gly Val Ile Thr
                165                 170                 175

Val Glu Glu Gly Lys Gly Leu Glu Asp Glu Leu Asp Val Val Glu Gly
            180                 185                 190

Met Gln Phe Asp Arg Gly Tyr Leu Ser Pro Tyr Phe Ile Asn Asn Gln
        195                 200                 205

Glu Lys Met Thr Val Glu Met Glu Asn Pro Leu Ile Leu Leu Val Asp
    210                 215                 220

Lys Lys Ile Asp Asn Leu Gln Glu Leu Leu Pro Ile Leu Glu Asn Val
225                 230                 235                 240

Ala Lys Ser Gly Arg Pro Leu Leu Ile Val Ala Glu Asp Val Glu Gly
                245                 250                 255

Gln Ala Leu Ala Thr Leu Val Val Asn Asn Leu Arg Gly Thr Phe Lys
            260                 265                 270

Val Ala Ala Val Lys Ala Pro Gly Phe Gly Asp Arg Arg Lys Ala Met
        275                 280                 285

Leu Gln Asp Leu Ala Ile Leu Thr Gly Gly Gln Val Ile Ser Glu Glu
    290                 295                 300

Leu Gly Met Ser Leu Glu Thr Ala Asp Pro Ser Ser Leu Gly Thr Ala
305                 310                 315                 320

Ser Lys Val Val Ile Asp Lys Glu Asn Thr Val Ile Val Asp Gly Ala
                325                 330                 335

Gly Thr Glu Ala Ser Val Asn Thr Arg Val Asp Gln Ile Arg Ala Glu
            340                 345                 350

Ile Glu Ser Ser Thr Ser Asp Tyr Asp Ile Glu Lys Leu Gln Glu Arg
        355                 360                 365

Val Ala Lys Leu Ala Gly Gly Val Ala Val Ile Lys Val Gly Ala Gly
    370                 375                 380

Ser Glu Met Glu Met Lys Glu Lys Lys Asp Arg Val Asp Asp Ala Leu
385                 390                 395                 400

His Ala Thr Arg Ala Ala Val Glu Glu Gly Val Val Ala Gly Gly Gly
                405                 410                 415

Val Ala Leu Ile Arg Ala Leu Ser Ser Val Thr Val Val Gly Asp Asn
            420                 425                 430

Glu Asp Gln Asn Val Gly Ile Ala Leu Ala Leu Arg Ala Met Glu Ala
        435                 440                 445

Pro Ile Arg Gln Ile Ala Gly Asn Ala Gly Ala Glu Gly Ser Val Val
    450                 455                 460

Val Asp Lys Val Lys Ser Gly Thr Gly Ser Phe Gly Phe Asn Ala Ser
465                 470                 475                 480

Thr Gly Glu Tyr Gly Asp Met Ile Ala Met Gly Ile Leu Asp Pro Ala
                485                 490                 495

Lys Val Thr Arg Ser Ser Leu Gln Ala Ala Ser Ile Ala Gly Leu
            500                 505                 510

Met Ile Thr Thr Glu Ala Met Val Ala Asp Ala Pro Val Glu Glu Gly
        515                 520                 525

Ala Gly Gly Met Pro Asp Met Gly Gly Met Gly Gly Met Gly Gly Met
    530                 535                 540

Pro Gly Met Met
```

545

<210> SEQ ID NO 3
<211> LENGTH: 2783
<212> TYPE: DNA
<213> ORGANISM: Oleispira antarctica

<400> SEQUENCE: 3

| | | | | | |
|---|---|---|---|---|---|
| atcaaaaaat | gcagcaagga | cagattcctg | cccaagaatt | agcagaaggt | ttcttgttag | 60 |
| cactggccgg | cgctttatta | ttaacgccgg | gttttgtcac | tgatgcgctg | ggttttacat | 120 |
| tactcgtccc | cgcgacgcgt | aaagcgttgg | tccataaggt | gattgcattt | attacccctc | 180 |
| gcatgatgac | tgcaagcagc | tttcaagcga | cgggtagttt | tcaggaaggc | tcgtttaaag | 240 |
| atgtacattc | gcacactgac | tcgcaaagca | gtcatgaaaa | atcacaatt | gaaggcgaat | 300 |
| ataccaaaga | cgataagtag | gtatttttc | ggctagccgt | tgaaatccta | gtaaaagccc | 360 |
| cgataaatta | accatctatt | tttcacagag | gcaatttagc | ctttgtttac | cttattgatc | 420 |
| ctaatacttg | ggatccaaca | gttggagagt | ctagcaaatg | aaaatccgtc | cattacatga | 480 |
| tcgtattgtt | gttcgccgta | aagaagaaga | gaccgcaact | gcgggtggta | ttatttacc | 540 |
| gggcgctgcg | gcagaaaaac | caaatcaagg | tgttgttatc | tctgtgggta | ctggccgtat | 600 |
| tcttgataat | ggttcagtgc | aagcgctggc | ggttaacgaa | ggcgatgttg | tcgttttgg | 660 |
| taaatactca | ggtcaaaata | ctatcgatat | cgatggtgaa | gaattattga | ttttgaatga | 720 |
| aagtgatatc | tacggcgttt | tagaagctta | attattacac | tcactttttt | atttaaccta | 780 |
| caaaatttaa | ggaaagatca | tggctgctaa | agacgtatta | tttggtgata | gcgcacgcgc | 840 |
| aaaaatgttg | gtaggtgtaa | acatttagc | cgacgcagta | agagttacct | taggacctaa | 900 |
| aggtcgtaac | gttgttatag | aaaaatcatt | tggtgcaccg | atcatcacca | agatggtgt | 960 |
| ttctgttgcg | cgtgaaatcg | aattgaaaga | caaattcgaa | acatgggcg | cacagatggt | 1020 |
| taaggaagtt | gcttctcaag | ccaacgacca | agccggtgac | ggcacaacga | cagcgactgt | 1080 |
| actagcacag | gcgattatca | gcgaaggctt | gaaatctgtt | gcggctggca | tgaatccaat | 1140 |
| ggatcttaaa | cgtggtattg | ataaagctac | ggctgctgtt | gttgccgcca | ttaaagaaca | 1200 |
| agctcagcct | tgcttggata | caaaagcaat | cgctcaggta | gggacaatct | ctgccaatgc | 1260 |
| cgatgaaacg | gttggtcgtt | taattgctga | agcgatggaa | aaagtcggta | agaaggtgt | 1320 |
| gattaccgtt | gaagaaggca | aaggccttga | gacagagctt | gatgttgtag | aaggcatgca | 1380 |
| gttcgatcgc | ggttacttgt | ctccgtactt | catcaacaac | caagaaaaaa | tgaccgtaga | 1440 |
| aatggaaaat | ccattaattc | tattggttga | taagaaaatt | gataaccttc | aagagctgtt | 1500 |
| gccaattctt | gaaaacgtcg | ctaaatcagg | tcgtccatta | ttgatcgttg | ctgaagatgt | 1560 |
| tgaaggccaa | gcactagcaa | cattggtagt | aaacaacttg | cgcggcacat | tcaaggttgc | 1620 |
| agcggttaaa | gcccctggtt | ttggcgatcg | tcgtaaagcg | atgttgcaag | atcttgccat | 1680 |
| cttgacgggt | ggtcaggtta | tttctgaaga | gctaggatg | tctttagaaa | ctgcggatcc | 1740 |
| ttcttctttg | ggtacggcaa | gcaaggttgt | tatcgataaa | gaaacaccg | tgattgttga | 1800 |
| tggcgcaggt | actgaagcaa | gcgttaatac | tcgtgttgac | cagatccgtg | ctgaaatcga | 1860 |
| aagctcgact | tctgattacg | acatcgaaaa | gttacaagaa | cgcgttgcta | agcttgcggg | 1920 |
| cggcgttgcc | gtgattaagg | ttggtgcggg | ttctgaaatg | gaaatgaaag | agaagaaaga | 1980 |
| ccgtgttgac | gatgcacttc | atgcaactcg | cgcagcggtt | gaagaaggtg | ttgttgcggg | 2040 |
| tggtggtgtt | gctttgatcc | gcgcactctc | ttcagtaacc | gttgttggtg | ataacgaaga | 2100 |

-continued

```
tcaaaacgtc ggtattgcat tggcacttcg tgcgatggaa gctcctatcc gtcaaatcgc    2160
gggtaacgca ggtgctgaag ggtcagtggt tgttgataaa gtgaaatctg cacaggtag     2220 ctttggtttt aacgccagca caggtgagta tggcgatatg attgcgatgg gtattttaga    2280
ccctgcaaaa gtcacgcgtt catctctaca agccgcggcg tctatcgcag gtttgatgat    2340
cacaaccgaa gccatggttg cggatgcgcc tgttgaagaa ggcgctggtg gtatgcctga    2400
tatgggcggc atgggtggaa tggcggtat gcctggcatg atgtaatcac tttgtgattc     2460
attgtcctga tctgcttacc gtgtaaaaag atcaggctca aggctgtctc tataaaaagc    2520
cgtatctttg atgagtgttg tctttctgct gaaaacgaca ttcttggagt gcggcttttt    2580
ttgattttgg tcataaaatt cagaatattg tgtaatttta tgtaactagc tggcctataa    2640
tgttgagttc ctctgggtgg catgatctca tggtacttca cttaagcctg attcactgcg    2700
gctttaacag taaataata acgcaacgta gaaacataat aagcgtatgg cattaatgaa     2760
gacggctgca tttaattcag atc                                            2783
```

<210> SEQ ID NO 4
<211> LENGTH: 333
<212> TYPE: PRT
<213> ORGANISM: Oleispira antarctica

<400> SEQUENCE: 4

```
Met Lys Asn Thr Leu Lys Ser Ser Arg Phe Ser Leu Lys Gln Leu
1               5                   10                  15

Gly Thr Gly Ala Leu Ile Ile Ser Ser Leu Phe Phe Gly Gly Cys Thr
                20                  25                  30

Thr Thr Gln Gln Asp Asn Leu Tyr Thr Gly Val Met Ser Leu Ala Arg
            35                  40                  45

Asp Ser Ala Gly Leu Glu Val Lys Thr Ala Ser Ala Gly Asp Val Asn
        50                  55                  60

Leu Thr Tyr Met Glu Arg Gln Gly Ser Asp Lys Asp Asn Ala Glu Ser
65                  70                  75                  80

Val Ile Leu Leu His Gly Phe Ser Ala Asp Lys Asp Asn Trp Ile Leu
                85                  90                  95

Phe Thr Lys Glu Phe Asp Glu Lys Tyr His Val Ile Ala Val Asp Leu
            100                 105                 110

Ala Gly His Gly Asp Ser Glu Gln Leu Leu Thr Thr Asp Tyr Gly Leu
        115                 120                 125

Ile Lys Gln Ala Glu Arg Leu Asp Ile Phe Leu Ser Gly Leu Gly Val
    130                 135                 140

Asn Ser Phe His Ile Ala Gly Asn Ser Met Gly Gly Ala Ile Ser Ala
145                 150                 155                 160

Ile Tyr Ser Leu Ser His Pro Glu Lys Val Lys Ser Leu Thr Leu Ile
                165                 170                 175

Asp Ala Ala Gly Val Asp Gly Asp Thr Glu Ser Glu Tyr Tyr Lys Val
            180                 185                 190

Leu Ala Glu Gly Lys Asn Pro Leu Ile Ala Thr Asp Glu Ala Ser Phe
        195                 200                 205

Glu Tyr Arg Met Gly Phe Thr Met Thr Gln Pro Pro Phe Leu Pro Trp
    210                 215                 220

Pro Leu Arg Pro Ser Leu Leu Arg Lys Thr Leu Ala Arg Ala Glu Ile
225                 230                 235                 240

Asn Asn Lys Ile Phe Ser Asp Met Leu Lys Thr Lys Glu Arg Leu Gly
```

-continued

```
                    245                 250                 255
Met Thr Asn Phe Gln Gln Lys Ile Glu Val Lys Met Ala Gln His Pro
            260                 265                 270

Leu Pro Thr Leu Ile Met Trp Gly Lys Glu Asp Arg Val Leu Asp Val
        275                 280                 285

Ser Ala Ala Ala Ala Phe Lys Lys Ile Ile Pro Gln Ala Thr Val His
    290                 295                 300

Ile Phe Pro Glu Val Gly His Leu Pro Met Val Glu Ile Pro Ser Glu
305                 310                 315                 320

Ser Ala Lys Val Tyr Glu Glu Phe Leu Ser Ser Ile Lys
                325                 330
```

<210> SEQ ID NO 5
<211> LENGTH: 3939
<212> TYPE: DNA
<213> ORGANISM: artificial sequence
<220> FEATURE:
<223> OTHER INFORMATION: DNA fragment from plasmid pBK1Est coding for esterase of Oleispira antarctica

<400> SEQUENCE: 5

| | | |
|---|---|---|
| acaggaaaca gctatgacct tgattacgcc aagctcgaaa ttaaccctca ctaaagggaa | 60 |
| caaaagctgg agctcgcgcg cctgcaggtc gacactagtg gatcaacggc gttcatggta | 120 |
| ctggctgagt tcagcgtcat aatgccgatg cgatactggc cgtcatgact gagtacttct | 180 |
| tctgctagca ccgattttc taatagcgca gcttctttta tttctgaacg ggcaactgat | 240 |
| gtagttttt tactaaccgg cttttaggc atggtaaact cttcgatatt caaaattatt | 300 |
| actgttcata ttacaatcat agtacaggct agaggcccaa aattgcagct gatattcacc | 360 |
| tttattattc taagcattat tacactcatc gcggtgttat taattgtgct aaataaaaat | 420 |
| acccgtagcg gaaaaattca gcaaatagcc aaagaaaacg attggcaata ccaagaattc | 480 |
| atcgattttg atgatgacat taagcaggca aactttggcc tattaaacta cagtcaaaat | 540 |
| gcaatttta gacatctcat tcaagcaact gacgaacact atggcttagc gtttaagacc | 600 |
| tttgactgtc gagcgttaga accttcaggt attcacaata gcagtcttat tttatttacc | 660 |
| ctcgcactaa agactgaatt caataaccta cacatttgct taagtcgaca tattcaagat | 720 |
| aaagatgcct tcactgacat cagtcaccaa caatcaatca acaccaata ccaatcgcaa | 780 |
| aaactcataa aactagccga tcaccaaatc ccaaaagcgt tcaaaaatga acgagcacg | 840 |
| tcacacaaaa tcaatttata cgctaacgaa ccaggtcaaa cttatcgttt ttttgagcac | 900 |
| gtttgttcca ctaatgaaag agaaaagtcg ttaattcact ggcttttggc gtatccgcac | 960 |
| cttcacatag aaattagtaa tggcatgcta ctggccttta aaaagaatca gttaattgaa | 1020 |
| gaaacctcgc ttatctcagc cattaccgct gtagccgaat ttgcgcttat cctcagccat | 1080 |
| gattaaactg acgccaatta atataagaca tactaattaa taactccctt aattgagaag | 1140 |
| aataatgaaa acacactca atcctcatc acgttttagt ctgaaacaac tcggcaccgg | 1200 |
| cgctctgatt atctccagtt tgttcttcgg tggttgcacc acaacacaac aagataattt | 1260 |
| atacacaggg gttatgtctc ttgcgagaga cagcgctggc ctagaagtta aaacagcctc | 1320 |
| tgccggtgac gtcaatctta cttatatgga acgccaaggc agtgacaaag ataatgccga | 1380 |
| aagcgttatt ttattacacg gtttctctgc tgataaagat aactggattc ttttaccaa | 1440 |
| agaattcgat gaaaaatatc atgttatcgc tgtcgattta gcgggacatg gcgattcaga | 1500 |
| acaattatta acgactgatt acggtctcat aaaacaagcc gagcgtttag atatcttctt | 1560 |

```
atctggctta gggggttaact catttcacat cgccggtaat tcaatggggg gggctatcag    1620
cgcaatctac agtttgagtc acccagagaa agttaaaagt cttacattga tcgatgcagc    1680
aggtgtcgat ggcgatactg aaagcgaata ctacaaagtt ttggcagaag gtaagaatcc    1740
tttaattgca actgatgaag caagttttga ataccgcatg ggtttcacca tgactcagcc    1800
tcctttccta ccttggccac taagaccttc tttattacgt aaaacgctag cccgtgccga    1860
gatcaataac aaaattttt ccgatatgct gaaaaccaaa gaacgtttag gaatgactaa     1920
ctttcaacag aaaattgaag tgaaaatggc tcaacatcca ttgccaacac tgattatgtg    1980
gggcaaagaa gatcgcgttc ttgacgtatc cgcagcagcg gccttcaaaa aaataattcc    2040
acaagcaact gttcatattt ttcctgaagt aggccaccta cctatggtag aaattcctag    2100
tgaaagcgct aaagtttatg aagagttttt gtcctctatt aaataagagc acataatcat    2160
gactgactta taaacagcca agcatttaaa atgcttggct gtttatttta atggccaaat    2220
tattcaacga ccaagctctg cggtaaaatc gcagtgggtt tcttgttttc atcaacagca    2280
acaaacgtga ataccccgt aatcgcattt ttctgattat caaaatacat actttccacc     2340
agcatattaa cttcaacttt taaactcgtc cgccctacct ctataacact ggcagtcaat    2400
tcgacaatgg tacctgcggg aacaggatgc ttaaaatcga ttcgatcact gctgacggtt    2460
acgatgcttt gtcgagaaaa acgagtcgct gcaataaaag aaacctcatc catccactgc    2520
attgcagtgc caccgaataa cgtatcatga tgatttgttg tctctggaaa taccgcttta    2580
gaaatagtgg ttttttgatac cgcctttcgc tgcgcaataa tatcttctct gctaagagtt    2640
gcggatggca tacataaact cgcttgatta agattaataa taaatagtta acagtatatt    2700
gaactgaggg tctgaagaac tctaatacct ctgaagaact ttgaggccgc tagagagaaa    2760
agaccagtga taatatttca tcttgccatg agagcttatc atgaaagcct gtgcttaaaa    2820
tcaatcatta tatttattca tctttaattg aaataataacc aatatatttc atatataatt    2880
tcacactacc cttatctcac tagacttccc gcgcataggc gcaaacaatc aacgcaagtt    2940
cacaataaag cggttcgctg caacacatgc cctagcgtct aaagtagcac gcacaacact    3000
ggccagtcgt actagcccct ttgcgattcg tgcagacgag caacaagcgc tattaaactt    3060
acctaaattt ctaaccacca ccattggttc ttttccacaa actcaaaaaa ctcgtcaaat    3120
ccgcttgcaa tttaaacgcg atgacataga tctaatcgat tatcaaaccc gcattcaagc    3180
gctcattaaa aacgcaccac tggcaagaag ttctacctgc actgaccaat atgcaagcgg    3240
cggcggaaga gctgcctttg atcgatcaag aagaagggag cagcaaagag gaaaacaatc    3300
aaaaagagga gagcaatcaa ataaaaacga gttattgagg attttaattt taaaacaggt    3360
atattaatac cctctctcgt agtaaacaat gactgtattt acacaaaaat aaatagaggt    3420
ataccatgtc aaacatctgg tttgaagtac caaagattga agtattaaac cgtcaaatgg    3480
aaaatactgc ctgcagcaac ttaggcattc aaattacaga aattggcgat gattatatca    3540
ctggcacaat gccagcagat gcacgtacct tccagccaat gggactgatt catggcggct    3600
caaatgtatt gctggcagaa acactgggca gcatggcagc taactgctgt attaatttgt    3660
ctcaagaata ttgtgttggc caagaaatta acgccaacca catacgcggt gttcgttccg    3720
gcatagtgac tggcacagca acgctagtac acaaaggaag aacctcccag atttgggaaa    3780
ttcgcatcgt taacgatcca aagaattcaa aaagcttctc gagagtactt ctagagcggc    3840
cgcgggccca tcgattttcc acccgggtgg ggtaccaggt aagtgtaccc aattcgccct    3900
```
atagtgagtc gtattacaat tcactggccg tcgttttac 3939

<210> SEQ ID NO 6
<211> LENGTH: 97
<212> TYPE: PRT
<213> ORGANISM: artificial sequence
<220> FEATURE:
<223> OTHER INFORMATION: cpn10 of Oleispira antarctica

<400> SEQUENCE: 6

```
Met Lys Ile Arg Pro Leu His Asp Arg Ile Val Val Arg Lys Glu
1               5                   10                  15

Glu Glu Thr Ala Thr Ala Gly Gly Ile Ile Leu Pro Gly Ala Ala
                20                  25                  30

Glu Lys Pro Asn Gln Gly Val Val Ile Ser Val Gly Thr Gly Arg Ile
                35                  40                  45

Leu Asp Asn Gly Ser Val Gln Ala Leu Ala Val Asn Glu Gly Asp Val
50                  55                  60

Val Val Phe Gly Lys Tyr Ser Gly Gln Asn Thr Ile Asp Ile Asp Gly
65                  70                  75                  80

Glu Glu Leu Leu Ile Leu Asn Glu Ser Asp Ile Tyr Gly Val Leu Glu
                85                  90                  95

Ala
```

<210> SEQ ID NO 7
<211> LENGTH: 548
<212> TYPE: PRT
<213> ORGANISM: artificial sequence
<220> FEATURE:
<223> OTHER INFORMATION: Cpn60 of Oleispira antarctica

<400> SEQUENCE: 7

```
Met Ala Ala Lys Asp Val Leu Phe Gly Asp Ser Ala Arg Ala Lys Met
1               5                   10                  15

Leu Val Gly Val Asn Ile Leu Ala Asp Ala Val Arg Val Thr Leu Gly
                20                  25                  30

Pro Lys Gly Arg Asn Val Val Ile Glu Lys Ser Phe Gly Ala Pro Ile
                35                  40                  45

Ile Thr Lys Asp Gly Val Ser Val Ala Arg Glu Ile Glu Leu Lys Asp
50                  55                  60

Lys Phe Glu Asn Met Gly Ala Gln Met Val Lys Glu Val Ala Ser Gln
65                  70                  75                  80

Ala Asn Asp Gln Ala Gly Asp Gly Thr Thr Thr Ala Thr Val Leu Ala
                85                  90                  95

Gln Ala Ile Ile Ser Glu Gly Leu Lys Ser Val Ala Ala Gly Met Asn
                100                 105                 110

Pro Met Asp Leu Lys Arg Gly Ile Asp Lys Ala Thr Ala Ala Val Val
                115                 120                 125

Ala Ala Ile Lys Glu Gln Ala Gln Pro Cys Leu Asp Thr Lys Ala Ile
130                 135                 140

Ala Gln Val Gly Thr Ile Ser Ala Asn Ala Asp Glu Thr Val Gly Arg
145                 150                 155                 160

Leu Ile Ala Glu Ala Met Glu Lys Val Gly Lys Glu Gly Val Ile Thr
                165                 170                 175

Val Glu Glu Gly Lys Gly Leu Glu Asp Glu Leu Asp Val Val Glu Gly
                180                 185                 190

Met Gln Phe Asp Arg Gly Tyr Leu Ser Pro Tyr Phe Ile Asn Asn Gln
```

```
                195                 200                 205
Glu Lys Met Thr Val Glu Met Glu Asn Pro Leu Ile Leu Leu Val Asp
            210                 215                 220

Lys Lys Ile Asp Asn Leu Gln Glu Leu Leu Pro Ile Leu Glu Asn Val
225                 230                 235                 240

Ala Lys Ser Gly Arg Pro Leu Leu Ile Val Ala Glu Asp Val Glu Gly
                245                 250                 255

Gln Ala Leu Ala Thr Leu Val Val Asn Asn Leu Arg Gly Thr Phe Lys
            260                 265                 270

Val Ala Ala Val Lys Ala Pro Gly Phe Gly Asp Arg Arg Lys Ala Met
            275                 280                 285

Leu Gln Asp Leu Ala Ile Leu Thr Gly Gly Gln Val Ile Ser Glu Glu
            290                 295                 300

Leu Gly Met Ser Leu Glu Thr Ala Asp Pro Ser Ser Leu Gly Thr Ala
305                 310                 315                 320

Ser Lys Val Val Ile Asp Lys Glu Asn Thr Val Ile Val Asp Gly Ala
                325                 330                 335

Gly Thr Glu Ala Ser Val Asn Thr Arg Val Asp Gln Ile Arg Ala Glu
            340                 345                 350

Ile Glu Ser Ser Thr Ser Asp Tyr Asp Ile Glu Lys Leu Gln Glu Arg
            355                 360                 365

Val Ala Lys Leu Ala Gly Gly Val Ala Val Ile Lys Val Gly Ala Gly
            370                 375                 380

Ser Glu Met Glu Met Lys Glu Lys Lys Asp Arg Val Asp Asp Ala Leu
385                 390                 395                 400

His Ala Thr Arg Ala Ala Val Glu Glu Gly Val Val Ala Gly Gly Gly
                405                 410                 415

Val Ala Leu Ile Arg Ala Leu Ser Ser Val Thr Val Val Gly Asp Asn
            420                 425                 430

Glu Asp Gln Asn Val Gly Ile Ala Leu Ala Leu Arg Ala Met Glu Ala
            435                 440                 445

Pro Ile Arg Gln Ile Ala Gly Asn Ala Gly Ala Glu Gly Ser Val Val
            450                 455                 460

Val Asp Lys Val Lys Ser Gly Thr Gly Ser Phe Gly Phe Asn Ala Ser
465                 470                 475                 480

Thr Gly Glu Tyr Gly Asp Met Ile Ala Met Gly Ile Leu Asp Pro Ala
                485                 490                 495

Lys Val Thr Arg Ser Ser Leu Gln Ala Ala Ala Ser Ile Ala Gly Leu
            500                 505                 510

Met Ile Thr Thr Glu Ala Met Val Ala Asp Ala Pro Val Glu Glu Gly
            515                 520                 525

Ala Gly Gly Met Pro Asp Met Gly Gly Met Gly Gly Met Gly Gly Met
            530                 535                 540

Pro Gly Met Met
545

<210> SEQ ID NO 8
<211> LENGTH: 333
<212> TYPE: PRT
<213> ORGANISM: Oleispira antarctica

<400> SEQUENCE: 8

Met Lys Asn Thr Leu Lys Ser Ser Ser Arg Phe Ser Leu Lys Gln Leu
1               5                   10                  15
```

```
Gly Thr Gly Ala Leu Ile Ile Ser Ser Leu Phe Phe Gly Gly Cys Thr
            20                  25                  30

Thr Thr Gln Gln Asp Asn Leu Tyr Thr Gly Val Met Ser Leu Ala Arg
        35                  40                  45

Asp Ser Ala Gly Leu Glu Val Lys Thr Ala Ser Ala Gly Asp Val Asn
    50                  55                  60

Leu Thr Tyr Met Glu Arg Gln Gly Ser Asp Lys Asp Asn Ala Glu Ser
65                  70                  75                  80

Val Ile Leu Leu His Gly Phe Ser Ala Asp Lys Asp Asn Trp Ile Leu
                85                  90                  95

Phe Thr Lys Glu Phe Asp Glu Lys Tyr His Val Ile Ala Val Asp Leu
            100                 105                 110

Ala Gly His Gly Asp Ser Glu Gln Leu Leu Thr Thr Asp Tyr Gly Leu
        115                 120                 125

Ile Lys Gln Ala Glu Arg Leu Asp Ile Phe Leu Ser Gly Leu Gly Val
    130                 135                 140

Asn Ser Phe His Ile Ala Gly Asn Ser Met Gly Gly Ala Ile Ser Ala
145                 150                 155                 160

Ile Tyr Ser Leu Ser His Pro Glu Lys Val Lys Ser Leu Thr Leu Ile
                165                 170                 175

Asp Ala Ala Gly Val Asp Gly Asp Thr Glu Ser Glu Tyr Tyr Lys Val
            180                 185                 190

Leu Ala Glu Gly Lys Asn Pro Leu Ile Ala Thr Asp Glu Ala Ser Phe
        195                 200                 205

Glu Tyr Arg Met Gly Phe Thr Met Thr Gln Pro Pro Phe Leu Pro Trp
    210                 215                 220

Pro Leu Arg Pro Ser Leu Leu Arg Lys Thr Leu Ala Arg Ala Glu Ile
225                 230                 235                 240

Asn Asn Lys Ile Phe Ser Asp Met Leu Lys Thr Lys Glu Arg Leu Gly
                245                 250                 255

Met Thr Asn Phe Gln Gln Lys Ile Glu Val Lys Met Ala Gln His Pro
            260                 265                 270

Leu Pro Thr Leu Ile Met Trp Gly Lys Glu Asp Arg Val Leu Asp Val
        275                 280                 285

Ser Ala Ala Ala Ala Phe Lys Lys Ile Ile Pro Gln Ala Thr Val His
    290                 295                 300

Ile Phe Pro Glu Val Gly His Leu Pro Met Val Glu Ile Pro Ser Glu
305                 310                 315                 320

Ser Ala Lys Val Tyr Glu Glu Phe Leu Ser Ser Ile Lys
                325                 330

<210> SEQ ID NO 9
<211> LENGTH: 5373
<212> TYPE: DNA
<213> ORGANISM: artificial sequence
<220> FEATURE:
<223> OTHER INFORMATION: fusion of native chaperonin-coding fragments
      with esterase of Oleispira antarctica

<400> SEQUENCE: 9
acaggaaaca gctatgacct tgattacgcc aagctcgaaa ttaaccctca ctaaagggaa      60
caaaagctgg agctcctaat acttgggatc aacagttgg  agagtctagc aaatgaaaat     120
ccgtccatta catgatcgta ttgttgttcg ccgtaaagaa gaagagaccg caactgcggg     180
tggtattatt ttaccgggcg ctgcggcaga aaaaccaaat caaggtgttg ttatctctgt     240
```

-continued

```
gggtactggc cgtattcttg ataatggttc agtgcaagcg ctggcggtta acgaaggcga    300
tgttgtcgtt tttggtaaat actcaggtca aaatactatc gatatcgatg gtgaagaatt    360
attgattttg aatgaaagtg atatctacgg cgttttagaa gcttaattat tacactcact    420
tttttattta acctacaaaa tttaaggaaa gatcatggct gctaaagacg tattatttgg    480
tgatagcgca cgcgcaaaaa tgttggtagg tgtaaacatt ttagccgacg cagtaagagt    540
taccttagga cctaaaggtc gtaacgttgt tatagaaaaa tcatttggtg caccgatcat    600
caccaaagat ggtgtttctg ttgcgcgtga atcgaattg aaagacaaat tcgaaaacat    660
gggcgcacag atggttaagg aagttgcttc tcaagccaac gaccaagccg gtgacggcac    720
aacgacagcg actgtactag cacaggcgat tatcagcgaa ggcttgaaat ctgttgcggc    780
tggcatgaat ccaatggatc ttaaacgtgg tattgataaa gctacggctg ctgttgttgc    840
cgccattaaa gaacaagctc agccttgctt ggatacaaaa gcaatcgctc aggtagggac    900
aatctctgcc aatgccgatg aaacggttgg tcgtttaatt gctgaagcga tggaaaaagt    960
cggtaaagaa ggtgtgatta ccgttgaaga aggcaaaggc cttgaagacg agcttgatgt   1020
tgtagaaggc atgcagttcg atcgcggtta cttgtctccg tacttcatca acaaccaaga   1080
aaaaatgacc gtagaaatgg aaaatccatt aattctattg gttgataaga aaattgataa   1140
ccttcaagag ctgttgccaa ttcttgaaaa cgtcgctaaa tcaggtcgtc cattattgat   1200
cgttgctgaa gatgttgaag gccaagcact agcaacattg gtagtaaaca acttgcgcgg   1260
cacattcaag gttgcagcgg ttaaagcccc tggttttggc gatcgtcgta aagcgatgtt   1320
gcaagatctt gccatcttga cgggtggtca ggttatttct gaagagctag ggatgtcttt   1380
agaaactgcg gatccttctt ctttgggtac ggcaagcaag gttgttatcg ataaagaaaa   1440
caccgtgatt gttgatggcg caggtactga agcaagcgtt aatactcgtg ttgaccagat   1500
ccgtgctgaa atcgaaagct cgacttctga ttacgacatc gaaaagttac aagaacgcgt   1560
tgctaagctt gcgggcggcg ttgccgtgat taaggttggt gcgggttctg aaatggaaat   1620
gaaagagaag aaagaccgtg ttgacgatgc acttcatgca actcgcgcag cggttgaaga   1680
aggtgttgtt gcgggtggtg gtgttgcttt gattcgcgca ctctcttcag taaccgttgt   1740
tggtgataac gaagatcaaa acgtcggtat tgcattggca cttcgtgcga tggaagctcc   1800
tatccgtcaa atcgcgggta acgcaggtgc tgaagggtca gtggttgttg ataaagtgaa   1860
atctggcaca ggtagctttg gttttaacgc cagcacaggt gagtatggcg atatgattgc   1920
gatgggtatt ttagaccctg caaaagtcac gcgttcatct ctacaagccg cggcgtctat   1980
cgcaggtttg atgatcacaa ccgaagccat ggttgcggat gcgcctgttg aagaaggcgc   2040
tggtggtatg cctgatatgg gcggcatggg tggaatgggc ggtatgcctg gcatgatgta   2100
atcactttgt gattcattgt cctgatctgc ttaccgtgtc gacatattca agataaagat   2160
gccttcactg acatcagtca ccaacaatca atcaaacacc aataccaatc gcaaaaactc   2220
ataaaactag ccgatcacca aatcccaaaa gcgttcaaaa atgaaacgag cacgtcacac   2280
aaaatcaatt tatacgctaa cgaaccaggt caaacttatc gttttttga gcacgtttgt   2340 tccactaatg aaagagaaaa gtcgttaatt cactggcttt tggcgtatcc gcaccttcac   2400
atagaaatta gtaatggcat gctactggcc tttaaaaaga atcagttaat tgaagaaacc   2460
tcgcttatct cagccattac cgctgtagcc gaatttgcgc ttatcctcag ccatgattaa   2520
actgacgcca attaatataa gacatactaa ttaataactc ccttaattga gaagaataat   2580
gaaaaacaca ctcaaatcct catcacgttt tagtctgaaa caactcggca ccggcgctct   2640
```

-continued

```
gattatctcc agtttgttct tcggtggttg caccacaaca caacaagata atttatacac    2700
aggggttatg tctcttgcga gagacagcgc tggcctagaa gttaaaacag cctctgccgg    2760
tgacgtcaat cttacttata tggaacgcca aggcagtgac aaagataatg ccgaaagcgt    2820 tatttttatta cacggtttct ctgctgataa agataactgg attctttta ccaaagaatt    2880 cgatgaaaaa tatcatgtta tcgctgtcga tttagcggga catggcgatt cagaacaatt    2940
attaacgact gattacggtc tcataaaaca agccgagcgt ttagatatct tcttatctgg    3000
cttaggggtt aactcatttc acatcgccgg taattcaatg ggggggggcta tcagcgcaat    3060 ctacagtttg agtcacccag agaaagttaa aagtcttaca ttgatcgatg cagcaggtgt    3120
cgatggcgat actgaaagcg aatactacaa agttttggca gaaggtaaga tcctttaat    3180 tgcaactgat gaagcaagtt ttgaataccg catgggtttc accatgactc agcctccttt    3240
cctaccttgg ccactaagac cttctttatt acgtaaaacg ctagcccgtg ccgagatcaa    3300
taacaaaatt ttttccgata tgctgaaaac caaagaacgt ttaggaatga ctaactttca    3360
acagaaaatt gaagtgaaaa tggctcaaca tccattgcca acactgatta tgtggggcaa    3420
agaagatcgc gttcttgacg tatccgcagc agcggccttc aaaaaaataa ttccacaagc    3480
aactgttcat atttttcctg aagtaggcca cctacctatg gtagaaattc ctagtgaaag    3540
cgctaaagtt tatgaagagt ttttgtcctc tattaaataa gagcacataa tcatgactga    3600
cttataaaca gccaagcatt taaaatgctt ggctgtttat tttaatggcc aaattattca    3660
acgaccaagc tctgcggtaa aatcgcagtg ggtttcttgt tttcatcaac agcaacaaac    3720
gtgaaatacc ccgtaatcgc atttttctga ttatcaaaat acatactttc caccagcata    3780
ttaacttcaa cttttaaact cgtccgccct acctctataa cactggcagt caattcgaca    3840
atggtacctg cgggaacagg atgcttaaaa tcgattcgat cactgctgac ggttacgatg    3900 cttttgtcgag aaaaacgagt cgctgcaata aagaaacct catccatcca ctgcattgca    3960
gtgccaccga ataacgtatc atgatgattt gttgtctctg gaaataccgc tttagaaata    4020
gtggtttttg atacgcgctt tcgctgcgca ataatatctt ctctgctaag agttgcggat    4080
ggcatacata aactcgcttg attaagatta ataataaata gttaacagta tattgaactg    4140
agggtctgaa gaactctaat acctctgaag aactttgagg ccgctagaga gaaaagacca    4200
gtgataatat ttcatcttgc catgagagct tatcatgaaa gcctgtgctt aaaatcaatc    4260
attatattta ttcatcttta attgaaataa taccaatata tttcatatat aatttcacac    4320 taccttatc tcactagact tcccgcgcat aggcgcaaac aatcaacgca agttcacaat    4380
aaagcggttc gctgcaacac atgccctagc gtctaaagta gcacgcacaa cactggccag    4440
tcgtactagc cccttttgcga ttcgtgcaga cgagcaacaa gcgctattaa acttacctaa    4500
atttctaacc accaccattg gttcttttcc acaaactcaa aaaactcgtc aaatccgctt    4560
gcaatttaaa cgcgatgaca tagatctaat cgattatcaa acccgcattc aagcgctcat    4620
taaaaacgca ccactggcaa gaagttctac ctgcactgac caatatgcaa gcggcggcgg    4680
aagagctgcc tttgatcgat caagaagaag ggagcagcaa agaggaaaac aatcaaaaag    4740
aggagagcaa tcaaataaaa acgagttatt gaggatttta attttaaaac aggtatatta    4800
ataccctctc tcgtagtaaa caatgactgt atttacacaa aaataaatag aggtatacca    4860
tgtcaaacat ctggtttgaa gtaccaagaa ttgaagtatt aaaccgtcaa atggaaaata    4920
ctgcctgcag caacttaggc attcaaatta cagaaattgg cgatgattat atcactggca    4980
```

-continued

```
caatgccagc agatgcacgt accttccagc caatgggact gattcatggc ggctcaaatg      5040
tattgctggc agaaacactg ggcagcatgg cagctaactg ctgtattaat ttgtctcaag      5100
aatattgtgt tggccaagaa attaacgcca accacatacg cggtgttcgt tccggcatag      5160
tgactggcac agcaacgcta gtacacaaag gaagaacctc ccagatttgg gaaattcgca      5220
tcgttaacga tccaaagaat tcaaaaagct tctcgagagt acttctagag cggccgcggg      5280
cccatcgatt ttccacccgg gtggggtacc aggtaagtgt acccaattcg ccctatagtg      5340
agtcgtatta caattcactg gccgtcgttt tac                                   5373
```

<210> SEQ ID NO 10
<211> LENGTH: 97
<212> TYPE: PRT
<213> ORGANISM: artificial sequence
<220> FEATURE:
<223> OTHER INFORMATION: Cpn10 of Oleispira antarctica

<400> SEQUENCE: 10

```
Met Lys Ile Arg Pro Leu His Asp Arg Ile Val Val Arg Arg Lys Glu
1               5                   10                  15

Glu Glu Thr Ala Thr Ala Gly Gly Ile Ile Leu Pro Gly Ala Ala Ala
            20                  25                  30

Glu Lys Pro Asn Gln Gly Val Val Ile Ser Val Gly Thr Gly Arg Ile
        35                  40                  45

Leu Asp Asn Gly Ser Val Gln Ala Leu Ala Val Asn Glu Gly Asp Val
    50                  55                  60

Val Val Phe Gly Lys Tyr Ser Gly Gln Asn Thr Ile Asp Ile Asp Gly
65                  70                  75                  80

Glu Glu Leu Leu Ile Leu Asn Glu Ser Asp Ile Tyr Gly Val Leu Glu
                85                  90                  95

Ala
```

<210> SEQ ID NO 11
<211> LENGTH: 548
<212> TYPE: PRT
<213> ORGANISM: artificial sequence
<220> FEATURE:
<223> OTHER INFORMATION: mutant protein

<400> SEQUENCE: 11

```
Met Ala Ala Lys Asp Val Leu Phe Gly Asp Ser Ala Arg Ala Lys Met
1               5                   10                  15

Leu Val Gly Val Asn Ile Leu Ala Asp Ala Val Arg Val Thr Leu Gly
            20                  25                  30

Pro Lys Gly Arg Asn Val Val Ile Glu Lys Ser Phe Gly Ala Pro Ile
        35                  40                  45

Ile Thr Lys Asp Gly Val Ser Val Ala Arg Glu Ile Glu Leu Lys Asp
    50                  55                  60

Lys Phe Glu Asn Met Gly Ala Gln Met Val Lys Glu Val Ala Ser Gln
65                  70                  75                  80

Ala Asn Asp Gln Ala Gly Asp Gly Thr Thr Thr Ala Thr Val Leu Ala
                85                  90                  95

Gln Ala Ile Ile Ser Glu Gly Leu Lys Ser Val Ala Ala Gly Met Asn
            100                 105                 110

Pro Met Asp Leu Lys Arg Gly Ile Asp Lys Ala Thr Ala Ala Val Val
        115                 120                 125

Ala Ala Ile Lys Glu Gln Ala Gln Pro Cys Leu Asp Thr Lys Ala Ile
```

-continued

```
            130                 135                 140
Ala Gln Val Gly Thr Ile Ser Ala Asn Ala Asp Glu Thr Val Gly Arg
145                 150                 155                 160

Leu Ile Ala Glu Ala Met Glu Lys Val Gly Lys Glu Gly Val Ile Thr
                165                 170                 175

Val Glu Glu Gly Lys Gly Leu Glu Asp Glu Leu Asp Val Val Glu Gly
                180                 185                 190

Met Gln Phe Asp Arg Gly Tyr Leu Ser Pro Tyr Phe Ile Asn Asn Gln
                195                 200                 205

Glu Lys Met Thr Val Glu Met Glu Asn Pro Leu Ile Leu Leu Val Asp
210                 215                 220

Lys Lys Ile Asp Asn Leu Gln Glu Leu Leu Pro Ile Leu Glu Asn Val
225                 230                 235                 240

Ala Lys Ser Gly Arg Pro Leu Leu Ile Val Ala Glu Asp Val Glu Gly
                245                 250                 255

Gln Ala Leu Ala Thr Leu Val Val Asn Asn Leu Arg Gly Thr Phe Lys
                260                 265                 270

Val Ala Ala Val Lys Ala Pro Gly Phe Gly Asp Arg Arg Lys Ala Met
                275                 280                 285

Leu Gln Asp Leu Ala Ile Leu Thr Gly Gly Gln Val Ile Ser Glu Glu
                290                 295                 300

Leu Gly Met Ser Leu Glu Thr Ala Asp Pro Ser Ser Leu Gly Thr Ala
305                 310                 315                 320

Ser Lys Val Val Ile Asp Lys Glu Asn Thr Val Ile Val Asp Gly Ala
                325                 330                 335

Gly Thr Glu Ala Ser Val Asn Thr Arg Val Asp Gln Ile Arg Ala Glu
                340                 345                 350

Ile Glu Ser Ser Thr Ser Asp Tyr Asp Ile Glu Lys Leu Gln Glu Arg
                355                 360                 365

Val Ala Lys Leu Ala Gly Gly Val Ala Val Ile Lys Val Gly Ala Gly
                370                 375                 380

Ser Glu Met Glu Met Lys Glu Lys Lys Asp Arg Val Asp Asp Ala Leu
385                 390                 395                 400

His Ala Thr Arg Ala Ala Val Glu Glu Gly Val Val Ala Gly Gly Gly
                405                 410                 415

Val Ala Leu Ile Arg Ala Leu Ser Ser Val Thr Val Val Gly Asp Asn
                420                 425                 430

Glu Asp Gln Asn Val Gly Ile Ala Leu Ala Leu Arg Ala Met Glu Ala
                435                 440                 445

Pro Ile Arg Gln Ile Ala Gly Asn Ala Gly Ala Ala Gly Ala Ala Val
450                 455                 460

Val Asp Lys Val Lys Ser Gly Thr Gly Ser Phe Gly Phe Asn Ala Ser
465                 470                 475                 480

Thr Gly Glu Tyr Gly Asp Met Ile Ala Met Gly Ile Leu Asp Pro Ala
                485                 490                 495

Lys Val Thr Arg Ser Ser Leu Gln Ala Ala Ser Ile Ala Gly Leu
                500                 505                 510

Met Ile Thr Thr Glu Ala Met Val Ala Asp Ala Pro Val Glu Glu Gly
                515                 520                 525

Ala Gly Gly Met Pro Asp Met Gly Gly Met Gly Gly Met Gly Gly Met
                530                 535                 540

Pro Gly Met Met
545
```

<210> SEQ ID NO 12
<211> LENGTH: 333
<212> TYPE: PRT
<213> ORGANISM: Oleispira antarctica

<400> SEQUENCE: 12

```
Met Lys Asn Thr Leu Lys Ser Ser Arg Phe Ser Leu Lys Gln Leu
1               5                   10                  15

Gly Thr Gly Ala Leu Ile Ile Ser Ser Leu Phe Phe Gly Gly Cys Thr
                20                  25                  30

Thr Thr Gln Gln Asp Asn Leu Tyr Thr Gly Val Met Ser Leu Ala Arg
            35                  40                  45

Asp Ser Ala Gly Leu Glu Val Lys Thr Ala Ser Ala Gly Asp Val Asn
        50                  55                  60

Leu Thr Tyr Met Glu Arg Gln Gly Ser Asp Lys Asp Asn Ala Glu Ser
65                  70                  75                  80

Val Ile Leu Leu His Gly Phe Ser Ala Asp Lys Asp Asn Trp Ile Leu
                85                  90                  95

Phe Thr Lys Glu Phe Asp Glu Lys Tyr His Val Ile Ala Val Asp Leu
            100                 105                 110

Ala Gly His Gly Asp Ser Glu Gln Leu Leu Thr Thr Asp Tyr Gly Leu
        115                 120                 125

Ile Lys Gln Ala Glu Arg Leu Asp Ile Phe Leu Ser Gly Leu Gly Val
130                 135                 140

Asn Ser Phe His Ile Ala Gly Asn Ser Met Gly Gly Ala Ile Ser Ala
145                 150                 155                 160

Ile Tyr Ser Leu Ser His Pro Glu Lys Val Lys Ser Leu Thr Leu Ile
                165                 170                 175

Asp Ala Ala Gly Val Asp Gly Asp Thr Glu Ser Glu Tyr Tyr Lys Val
            180                 185                 190

Leu Ala Glu Gly Lys Asn Pro Leu Ile Ala Thr Asp Glu Ala Ser Phe
        195                 200                 205

Glu Tyr Arg Met Gly Phe Thr Met Thr Gln Pro Pro Phe Leu Pro Trp
210                 215                 220

Pro Leu Arg Pro Ser Leu Leu Arg Lys Thr Leu Ala Arg Ala Glu Ile
225                 230                 235                 240

Asn Asn Lys Ile Phe Ser Asp Met Leu Lys Thr Lys Glu Arg Leu Gly
                245                 250                 255

Met Thr Asn Phe Gln Gln Lys Ile Glu Val Lys Met Ala Gln His Pro
            260                 265                 270

Leu Pro Thr Leu Ile Met Trp Gly Lys Glu Asp Arg Val Leu Asp Val
        275                 280                 285

Ser Ala Ala Ala Phe Lys Lys Ile Ile Pro Gln Ala Thr Val His
290                 295                 300

Ile Phe Pro Glu Val Gly His Leu Pro Met Val Glu Ile Pro Ser Glu
305                 310                 315                 320

Ser Ala Lys Val Tyr Glu Glu Phe Leu Ser Ser Ile Lys
                325                 330
```

<210> SEQ ID NO 13
<211> LENGTH: 5373
<212> TYPE: DNA
<213> ORGANISM: artificial sequence
<220> FEATURE:
<223> OTHER INFORMATION: expression cassette for fusion protein

<400> SEQUENCE: 13

```
acaggaaaca gctatgacct tgattacgcc aagctcgaaa ttaaccctca ctaaagggaa    60
caaaagctgg agctcctaat acttgggatc caacagttgg agagtctagc aaatgaaaat   120
ccgtccatta catgatcgta ttgttgttcg ccgtaaagaa gaagagaccg caactgcggg   180
tggtattatt ttaccgggcg ctgcggcaga aaaaccaaat caaggtgttg ttatctctgt   240
gggtactggc cgtattcttg ataatggttc agtgcaagcg ctggcggtta acgaaggcga   300
tgttgtcgtt tttggtaaat actcaggtca aaatactatc gatatcgatg gtgaagaatt   360
attgattttg aatgaaagtg atatctacgg cgttttagaa gcttaattat tacactcact   420
tttttattta acctcaaaaa tttaaggaaa gatcatggct gctaaagacg tattatttgg   480
tgatagcgca cgcgcaaaaa tgttggtagg tgtaaacatt ttagccgacg cagtaagagt   540
taccttagga cctaaaggtc gtaacgttgt tatagaaaaa tcatttggtg caccgatcat   600
caccaaagat ggtgtttctg ttgcgcgtga atcgaattg aaagacaaat cgaaaacat    660
gggcgcacag atggttaagg aagttgcttc tcaagccaac gaccaagccg gtgacggcac   720
aacgacagcg actgtactag cacaggcgat tatcagcgaa ggcttgaaat ctgttgcggc   780
tggcatgaat ccaatggatc ttaaacgtgg tattgataaa gctacggctg ctgttgttgc   840
cgccattaaa gaacaagctc agccttgctt ggatacaaaa gcaatcgctc aggtagggac   900
aatctctgcc aatgccgatg aaacggttgg tcgtttaatt gctgaagcga tggaaaaagt   960
cggtaaagaa ggtgtgatta ccgttgaaga aggcaaaggc cttgaagacg agcttgatgt  1020
tgtagaaggc atgcagttcg atcgcggtta cttgtctccg tacttcatca acaaccaaga  1080
aaaaatgacc gtagaaatgg aaaatccatt aattctattg gttgataaga aaattgataa  1140
ccttcaagag ctgttgccaa ttcttgaaaa cgtcgctaaa tcaggtcgtc cattattgat  1200
cgttgctgaa gatgttgaag gccaagcact agcaacattg gtagtaaaca acttgcgcgg  1260
cacattcaag gttgcagcgg ttaaagcccc tggttttggc gatcgtcgta agcgatgtt   1320
gcaagatctt gccatcttga cgggtggtca ggttatttct gaagagctag ggatgtcttt  1380
agaaactgcg gatccttctt ctttgggtac ggcaagcaag gttgttatcg ataaagaaaa  1440
caccgtgatt gttgatggcg caggtactga agcaagcgtt aatactcgtg ttgaccagat  1500
ccgtgctgaa atcgaaagct cgacttctga ttacgacatc gaaaagttac aagaacgcgt  1560
tgctaagctt gcgggcggcg ttgccgtgat taaggttggt gcgggttctg aaatggaaat  1620
gaaagagaag aaagaccgtg ttgacgatgc acttcatgca actcgcgcag cggttgaaga  1680
aggtgttgtt gcgggtggtg gtgttgcttt gattcgcgca ctctcttcag taaccgttgt  1740
tggtgataac gaagatcaaa acgtcggtat tgcattggca cttcgtgcga tggaagctcc  1800
tatccgtcaa atcgcgggta acgcaggtgc tgcaggggca gcggttgttg ataaagtgaa  1860
atctggcaca ggtagctttg gttttaacgc cagcacaggt gagtatggcg atatgattgc  1920
gatgggtatt ttagaccctg caaaagtcac gcgttcatct ctacaagccg cggcgtctat  1980
cgcaggttg atgatcacaa ccgaagccat ggttgcggat gcgcctgttg aagaaggcgc  2040
tggtggtatg cctgatatgg gcggcatggg tggaatgggc ggtatgcctg gcatgatgta  2100
atcactttgt gattcattgt cctgatctgc ttaccgtgtc gacatattca agataaagat  2160
gccttcactg acatcagtca ccaacaatca atcaaacacc aataccaatc gcaaaaactc  2220
ataaaactag ccgatcacca aatcccaaaa gcgttcaaaa atgaaacgag cacgtcacac  2280
```

```
aaaatcaatt tatacgctaa cgaaccaggt caaacttatc gttttttgtga gcacgtttgt    2340 tccactaatg aaagagaaaa gtcgttaatt cactggcttt tggcgtatcc gcaccttcac    2400
atagaaatta gtaatggcat gctactggcc tttaaaaaga atcagttaat tgaagaaacc    2460
tcgcttatct cagccattac cgctgtagcc gaatttgcgc ttatcctcag ccatgattaa    2520
actgacgcca attaatataa gacatactaa ttaataactc ccttaattga gaagaataat    2580
gaaaaacaca ctcaaatcct catcacgttt tagtctgaaa caactcggca ccggcgctct    2640
gattatctcc agtttgttct tcggtggttg caccacaaca caacaagata atttatacac    2700
aggggttatg tctcttgcga gagacagcgc tggcctagaa gttaaaacag cctctgccgg    2760
tgacgtcaat cttacttata tggaacgcca aggcagtgac aaagataatg ccgaaagcgt    2820
tattttatta cacggtttct ctgctgataa agataactgg attcttttta ccaaagaatt    2880
cgatgaaaaa tatcatgtta tcgctgtcga tttagcggga catggcgatt cagaacaatt    2940
attaacgact gattacggtc tcataaaaca agccgagcgt ttagatatct tcttatctgg    3000
cttaggggtt aactcatttc acatcgccgg taattcaatg ggggggggcta tcagcgcaat    3060 ctacagtttg agtcacccag agaaagttaa aagtcttaca ttgatcgatg cagcaggtgt    3120
cgatggcgat actgaaagcg aatactacaa agttttggca gaaggtaaga atcctttaat    3180
tgcaactgat gaagcaagtt ttgaataccg catgggtttc accatgactc agcctccttt    3240
cctaccttgg ccactaagac cttctttatt acgtaaaacg ctagcccgtg ccgagatcaa    3300
taacaaaatt ttttccgata tgctgaaaac caaagaacgt ttaggaatga ctaactttca    3360
acagaaaatt gaagtgaaaa tggctcaaca tccattgcca acactgatta tgtggggcaa    3420
agaagatcgc gttcttgacg tatccgcagc agcggccttc aaaaaaataa ttccacaagc    3480
aactgttcat attttttcctg aagtaggcca cctacctatg gtagaaattc ctagtgaaag    3540
cgctaaagtt tatgaagagt ttttgtcctc tattaaataa gagcacataa tcatgactga    3600
cttataaaca gccaagcatt taaaatgctt ggctgtttat tttaatggcc aaattattca    3660
acgaccaagc tctgcggtaa aatcgcagtg ggtttcttgt tttcatcaac agcaacaaac    3720
gtgaaatacc ccgtaatcgc attttttctga ttatcaaaat acatactttc caccagcata    3780
ttaacttcaa cttttaaact cgtccgccct acctctataa cactggcagt caattcgaca    3840
atggtacctg cgggaacagg atgcttaaaa tcgattcgat cactgctgac ggttacgatg    3900
ctttgtcgag aaaaacgagt cgctgcaata aagaaaacct catccatcca ctgcattgca    3960
gtgccaccga ataacgtatc atgatgattt gttgtctctg gaaataccgc tttagaaata    4020 gtggttttg atacgcgctt tcgctgcgca ataatatctt ctctgctaag agttgcggat    4080
ggcatacata aactcgcttg attaagatta ataataaata gttaacagta tattgaactg    4140
agggtctgaa gaactctaat acctctgaag aactttgagg ccgctagaga gaaaagacca    4200
gtgataatat ttcatcttgc catgagagct tatcatgaaa gcctgtgctt aaaatcaatc    4260
attatattta ttcatctttta attgaaataa taccaatata tttcatatat aatttcacac    4320
tacccttatc tcactagact tcccgcgcat aggcgcaaac aatcaacgca agttcacaat    4380
aaagcggttc gctgcaacac atgccctagc gtctaaagta gcacgcacaa cactggccag    4440
tcgtactagc cccttttgcga ttcgtgcaga cgagcaacaa cgctattaa acttacctaa    4500 atttctaacc accaccattg gttcttttcc acaaactcaa aaaactcgtc aaatccgctt    4560
gcaatttaaa cgcgatgaca tagatctaat cgattatcaa acccgcattc aagcgctcat    4620
taaaaacgca ccactggcaa gaagttctac ctgcactgac caatatgcaa gcggcggcgg    4680
```

| | |
|---|---|
| aagagctgcc tttgatcgat caagaagaag ggagcagcaa agaggaaaac aatcaaaaag | 4740 |
| aggagagcaa tcaaataaaa acgagttatt gaggatttta attttaaaac aggtatatta | 4800 |
| ataccctctc tcgtagtaaa caatgactgt atttacacaa aaataaatag aggtatacca | 4860 |
| tgtcaaacat ctggtttgaa gtaccaaaga ttgaagtatt aaaccgtcaa atggaaaata | 4920 |
| ctgcctgcag caacttaggc attcaaatta cagaaattgg cgatgattat atcactggca | 4980 |
| caatgccagc agatgcacgt accttccagc caatgggact gattcatggc ggctcaaatg | 5040 |
| tattgctggc agaaacactg ggcagcatgg cagctaactg ctgtattaat ttgtctcaag | 5100 |
| aatattgtgt tggccaagaa attaacgcca accacatacg cggtgttcgt tccggcatag | 5160 |
| tgactggcac agcaacgcta gtacacaaag gaagaacctc ccagatttgg gaaattcgca | 5220 |
| tcgttaacga tccaaagaat tcaaaaagct tctcgagagt acttctagag cggccgcggg | 5280 |
| cccatcgatt ttccacccgg gtggggtacc aggtaagtgt acccaattcg ccctatagtg | 5340 |
| agtcgtatta caattcactg gccgtcgttt tac | 5373 |

<210> SEQ ID NO 14
<211> LENGTH: 97
<212> TYPE: PRT
<213> ORGANISM: artificial sequence
<220> FEATURE:
<223> OTHER INFORMATION: Cpn10 of Oleispira antarctica

<400> SEQUENCE: 14

```
Met Lys Ile Arg Pro Leu His Asp Arg Ile Val Val Arg Arg Lys Glu
1               5                  10                  15

Glu Glu Thr Ala Thr Ala Gly Gly Ile Ile Leu Pro Gly Ala Ala Ala
            20                  25                  30

Glu Lys Pro Asn Gln Gly Val Val Ile Ser Val Gly Thr Gly Arg Ile
        35                  40                  45

Leu Asp Asn Gly Ser Val Gln Ala Leu Ala Val Asn Glu Gly Asp Val
    50                  55                  60

Val Val Phe Gly Lys Tyr Ser Gly Gln Asn Thr Ile Asp Ile Asp Gly
65                  70                  75                  80

Glu Glu Leu Leu Ile Leu Asn Glu Ser Asp Ile Tyr Gly Val Leu Glu
                85                  90                  95

Ala
```

<210> SEQ ID NO 15
<211> LENGTH: 548
<212> TYPE: PRT
<213> ORGANISM: artificial sequence
<220> FEATURE:
<223> OTHER INFORMATION: Cpn60 of Oleispira antarctica

<400> SEQUENCE: 15

```
Met Ala Ala Lys Asp Val Leu Phe Gly Asp Ser Ala Arg Ala Lys Met
1               5                  10                  15

Leu Val Gly Val Asn Ile Leu Ala Asp Ala Val Arg Val Thr Leu Gly
            20                  25                  30

Pro Lys Gly Arg Asn Val Val Ile Glu Lys Ser Phe Gly Ala Pro Ile
        35                  40                  45

Ile Thr Lys Asp Gly Val Ser Val Ala Arg Glu Ile Glu Leu Lys Asp
    50                  55                  60

Lys Phe Glu Asn Met Gly Ala Gln Met Val Lys Glu Val Ala Ser Gln
65                  70                  75                  80
```

```
Ala Asn Asp Gln Ala Gly Asp Gly Thr Thr Thr Ala Thr Val Leu Ala
                85                  90                  95

Gln Ala Ile Ile Ser Glu Gly Leu Lys Ser Val Ala Ala Gly Met Asn
            100                 105                 110

Pro Met Asp Leu Lys Arg Gly Ile Asp Lys Ala Thr Ala Ala Val Val
            115                 120                 125

Ala Ala Ile Lys Glu Gln Ala Gln Pro Cys Leu Asp Thr Lys Ala Ile
            130                 135                 140

Ala Gln Val Gly Thr Ile Ser Ala Asn Ala Asp Glu Thr Val Gly Arg
145                 150                 155                 160

Leu Ile Ala Glu Ala Met Glu Lys Val Gly Lys Glu Gly Val Ile Thr
                165                 170                 175

Val Glu Glu Gly Lys Gly Leu Glu Asp Glu Leu Asp Val Val Glu Gly
            180                 185                 190

Met Gln Phe Asp Arg Gly Tyr Leu Ser Pro Tyr Phe Ile Asn Asn Gln
            195                 200                 205

Glu Lys Met Thr Val Glu Met Glu Asn Pro Leu Ile Leu Leu Val Asp
            210                 215                 220

Lys Lys Ile Asp Asn Leu Gln Glu Leu Leu Pro Ile Leu Glu Asn Val
225                 230                 235                 240

Ala Lys Ser Gly Arg Pro Leu Leu Ile Val Ala Glu Asp Val Glu Gly
                245                 250                 255

Gln Ala Leu Ala Thr Leu Val Val Asn Asn Leu Arg Gly Thr Phe Lys
            260                 265                 270

Val Ala Val Lys Ala Pro Gly Phe Gly Asp Arg Arg Lys Ala Met
            275                 280                 285

Leu Gln Asp Leu Ala Ile Leu Thr Gly Gly Gln Val Ile Ser Glu Glu
            290                 295                 300

Leu Gly Met Ser Leu Glu Thr Ala Asp Pro Ser Ser Leu Gly Thr Ala
305                 310                 315                 320

Ser Lys Val Val Ile Asp Lys Glu Asn Thr Val Ile Val Asp Gly Ala
                325                 330                 335

Gly Thr Glu Ala Ser Val Asn Thr Arg Val Asp Gln Ile Arg Ala Glu
            340                 345                 350

Ile Glu Ser Ser Thr Ser Asp Tyr Asp Ile Glu Lys Leu Gln Glu Arg
            355                 360                 365

Val Ala Lys Leu Ala Gly Gly Val Ala Val Ile Lys Val Gly Ala Gly
            370                 375                 380

Ser Glu Met Glu Met Lys Glu Lys Lys Asp Arg Val Asp Asp Ala Leu
385                 390                 395                 400

His Ala Thr Arg Ala Ala Val Glu Glu Gly Val Val Ala Gly Gly
                405                 410                 415

Val Ala Leu Ile Arg Ala Leu Ser Ser Val Thr Val Val Gly Asp Asn
            420                 425                 430

Glu Asp Gln Asn Val Gly Ile Ala Leu Ala Leu Arg Ala Met Glu Ala
            435                 440                 445

Pro Ile Arg Gln Ile Ala Gly Asn Ala Gly Ala Ala Gly Ala Ala Val
            450                 455                 460

Val Asp Lys Val Lys Ser Gly Thr Gly Ser Phe Gly Phe Asn Ala Ser
465                 470                 475                 480

Thr Gly Glu Tyr Gly Asp Met Ile Ala Met Gly Ile Leu Asp Pro Ala
                485                 490                 495
```

```
Lys Val Thr Arg Ser Ser Leu Gln Ala Ala Ala Ser Ile Ala Gly Leu
                500                 505                 510
Met Ile Thr Thr Glu Ala Met Val Ala Asp Ala Pro Val Glu Glu Gly
            515                 520                 525
Ala Gly Gly Met Pro Asp Met Gly Gly Met Gly Gly Met Gly Gly Met
        530                 535                 540
Pro Gly Met Met
545

<210> SEQ ID NO 16
<211> LENGTH: 2783
<212> TYPE: DNA
<213> ORGANISM: artificial sequence
<220> FEATURE:
<223> OTHER INFORMATION: coding sequence encoding mutant protein

<400> SEQUENCE: 16
```

| | | | | | |
|---|---|---|---|---|---|
| atcaaaaaat | gcagcaagga | cagattcctg | cccaagaatt | agcagaaggt | ttcttgttag | 60 |
| cactggccgg | cgcttttatta | ttaacgccgg | gttttgtcac | tgatgcgctg | gttttacat | 120 |
| tactcgtccc | cgcgacgcgt | aaagcgttgg | tccataaggt | gattgcattt | attacccctc | 180 |
| gcatgatgac | tgcaagcagc | tttcaagcga | cgggtagttt | tcaggaaggc | tcgtttaaag | 240 |
| atgtacattc | gcacactgac | tcgcaaagca | gtcatgaaaa | aatcacaatt | gaaggcgaat | 300 |
| ataccaaaga | cgataagtag | gtattttttc | ggctagccgt | tgaaatccta | gtaaaagccc | 360 |
| cgataaatta | accatctatt | tttcacagag | gcaatttagc | cttttgtttac | cttattgatc | 420 |
| ctaatacttg | ggatccaaca | gttggagagt | ctagcaaatg | aaaatccgtc | cattacatga | 480 |
| tcgtattgtt | gttcgccgta | aagaagaaga | gaccgcaact | gcgggtggta | ttatttttacc | 540 |
| gggcgctgcg | gcagaaaaac | caaatcaagg | tgttgttatc | tctgtgggta | ctggccgtat | 600 |
| tcttgataat | ggttcagtgc | aagcgctggc | ggttaacgaa | ggcgatgttg | tcgttttttgg | 660 |
| taaatactca | ggtcaaaata | ctatcgatat | cgatggtgaa | gaattattga | ttttgaatga | 720 |
| aagtgatatc | tacggcgttt | tagaagctta | attattacac | tcactttttt | atttaaccta | 780 |
| caaaatttaa | ggaaagatca | tggctgctaa | agacgtatta | tttggtgata | gcgcacgcgc | 840 |
| aaaaatgttg | gtaggtgtaa | acatttttagc | cgacgcagta | agagttacct | taggacctaa | 900 |
| aggtcgtaac | gttgttatag | aaaaatcatt | tggtgcaccg | atcatcacca | agatggtgt | 960 |
| ttctgttgcg | cgtgaaatcg | aattgaaaga | caaattcgaa | acatgggcg | cacagatggt | 1020 |
| taaggaagtt | gcttctcaag | ccaacgacca | agccggtgac | ggcacaacga | cagcgactgt | 1080 |
| actagcacag | gcgattatca | gcgaaggctt | gaaatctgtt | gcggctggca | tgaatccaat | 1140 |
| ggatcttaaa | cgtggtattg | ataaagctac | ggctgctgtt | gttgccgcca | ttaaagaaca | 1200 |
| agctcagcct | tgcttggata | caaaagcaat | cgctcaggta | gggacaatct | ctgccaatgc | 1260 |
| cgatgaaacg | gttggtcgtt | taattgctga | agcgatggaa | aaagtcggta | agaaggtgt | 1320 |
| gattaccgtt | gaagaaggca | aaggccttga | agacgagctt | gatgttgtag | aaggcatgca | 1380 |
| gttcgatcgc | ggttacttgt | ctccgtactt | catcaacaac | caagaaaaaa | tgaccgtaga | 1440 |
| aatggaaaat | ccattaattc | tattggttga | taagaaaatt | gataaccttc | aagagctgtt | 1500 |
| gccaattctt | gaaacgtcg | ctaaatcagg | tcgtccatta | ttgatcgttg | ctgaagatgt | 1560 |
| tgaaggccaa | gcactagcaa | cattggtagt | aaacaacttg | cgcggcacat | tcaaggttgc | 1620 |
| agcggttaaa | gccctggtt | ttggcgatcg | tcgtaaagcg | atgttgcaag | atcttgccat | 1680 |
| cttgacgggt | ggtcaggtta | tttctgaaga | gctagggatg | tctttagaaa | ctgcggatcc | 1740 |

-continued

```
ttcttctttg ggtacggcaa gcaaggttgt tatcgataaa gaaaacaccg tgattgttga    1800
tggcgcaggt actgaagcaa gcgttaatac tcgtgttgac cagatccgtg ctgaaatcga    1860
aagctcgact tctgattacg acatcgaaaa gttacaagaa cgcgttgcta agcttgcggg    1920
cggcgttgcc gtgattaagg ttggtgcggg ttctgaaatg gaaatgaaag agaagaaaga    1980
ccgtgttgac gatgcacttc atgcaactcg cgcagcggtt gaagaaggtg ttgttgcggg    2040
tggtggtgtt gctttgattc gcgcactctc ttcagtaacc gttgttggtg ataacgaaga    2100
tcaaaacgtc ggtattgcat tggcacttcg tgcgatggaa gctcctatcc gtcaaatcgc    2160
gggtaacgca ggtgctgcag ggcagcggt tgttgataaa gtgaaatctg cacaggtag     2220 ctttggtttt aacgccagca caggtgagta tggcgtatg attgcgatgg gtattttaga    2280
ccctgcaaaa gtcacgcgtt catctctaca agccgcggcg tctatcgcag gtttgatgat    2340
cacaaccgaa gccatggttg cggatgcgcc tgttgaagaa ggcgctggtg gtatgcctga    2400
tatgggcggc atgggtggaa tggcggtat gcctggcatg atgtaatcac tttgtgattc    2460
attgtcctga tctgcttacc gtgtaaaaag atcaggctca aggctgtctc tataaaaagc    2520
cgtatctttg atgagtgttg tctttctgct gaaaacgaca ttcttggagt gcggcttttt    2580
ttgattttgg tcataaaatt cagaatattg tgtaatttta tgtaactagc tggcctataa    2640
tgttgagttc ctctgggtgg catgatctca tggtacttca cttaagcctg attcactgcg    2700
gctttaacag taaataata acgcaacgta gaaacataat aagcgtatgg cattaatgaa    2760
gacggctgca tttaattcag atc                                            2783
```

<210> SEQ ID NO 17
<211> LENGTH: 22
<212> TYPE: DNA
<213> ORGANISM: artificial sequence
<220> FEATURE:
<223> OTHER INFORMATION: Forward Primer
<220> FEATURE:
<221> NAME/KEY: misc_feature
<222> LOCATION: (1)..(22)
<223> OTHER INFORMATION: "n" defines inosine

<400> SEQUENCE: 17
gcngcnggna tgaayccnat gg                                              22

<210> SEQ ID NO 18
<211> LENGTH: 23
<212> TYPE: DNA
<213> ORGANISM: artificial sequence
<220> FEATURE:
<223> OTHER INFORMATION: Reverse Primer
<220> FEATURE:
<221> NAME/KEY: misc_feature
<222> LOCATION: (1)..(23)
<223> OTHER INFORMATION: residue "n" designates inosine

<400> SEQUENCE: 18
ccnccnccng cnacnacncc ytc                                             23

<210> SEQ ID NO 19
<211> LENGTH: 13
<212> TYPE: PRT
<213> ORGANISM: Oleispira antarctica

<400> SEQUENCE: 19

Ser Val Ala Ala Gly Met Asn Pro Met Asp Leu Gln Arg
1               5                   10

-continued

<210> SEQ ID NO 20
<211> LENGTH: 16
<212> TYPE: PRT
<213> ORGANISM: Oleispira antarctica

<400> SEQUENCE: 20

Val Glu Glu Gly Val Val Ala Gly Gly Gly Val Ala Ala Leu Leu Arg
1               5                   10                  15

<210> SEQ ID NO 21
<211> LENGTH: 42
<212> TYPE: DNA
<213> ORGANISM: artificial sequence
<220> FEATURE:
<223> OTHER INFORMATION: Oligonucleotide

<400> SEQUENCE: 21
ggtggtcagt ggttgttgtt gatacagtga atctggcac ag                              42

<210> SEQ ID NO 22
<211> LENGTH: 37
<212> TYPE: DNA
<213> ORGANISM: artificial sequence
<220> FEATURE:
<223> OTHER INFORMATION: Oligonucleotide

<400> SEQUENCE: 22
cctgtgccag atttcactgt atcaacaacc actgacc                                   37

<210> SEQ ID NO 23
<211> LENGTH: 30
<212> TYPE: DNA
<213> ORGANISM: artificial sequence
<220> FEATURE:
<223> OTHER INFORMATION: Oligonucleotide

<400> SEQUENCE: 23
ggtgataaag tgaaaggtgg cacaggtagc                                           30

<210> SEQ ID NO 24
<211> LENGTH: 30
<212> TYPE: DNA
<213> ORGANISM: artificial sequence
<220> FEATURE:
<223> OTHER INFORMATION: Oligonucleotide

<400> SEQUENCE: 24
gctacctgtg ccacctttca ctttatcaac                                           30

<210> SEQ ID NO 25
<211> LENGTH: 46
<212> TYPE: DNA
<213> ORGANISM: artificial sequence
<220> FEATURE:
<223> OTHER INFORMATION: Oligonucleotide

<400> SEQUENCE: 25
ggtcagtggt tgttgataca gtgaaaggtg gcacaggtag ctttgg                         46

<210> SEQ ID NO 26
<211> LENGTH: 46
<212> TYPE: DNA
<213> ORGANISM: artificial sequence
<220> FEATURE:
<223> OTHER INFORMATION: Oligonucleotide

```
<400> SEQUENCE: 26
ccaaagctac ctgtgccacc tttcactgta tcaacaacca ctgacc                    46

<210> SEQ ID NO 27
<211> LENGTH: 42
<212> TYPE: DNA
<213> ORGANISM: artificial sequence
<220> FEATURE:
<223> OTHER INFORMATION: Oligonucleotide

<400> SEQUENCE: 27
cctaacgcag gtgctgcagg ggcagcggtt gttgataaag tg                        42

<210> SEQ ID NO 28
<211> LENGTH: 42
<212> TYPE: DNA
<213> ORGANISM: artificial sequence
<220> FEATURE:
<223> OTHER INFORMATION: Oligonucleotide

<400> SEQUENCE: 28
ctctttatca acaaccgctg cccctgcagc acctgcgtta cc                        42
```